(12) United States Patent
Frey et al.

(10) Patent No.: US 8,702,921 B2
(45) Date of Patent: Apr. 22, 2014

(54) BIOSENSORS ARRAY AND METHOD FOR OPERATING A BIOSENSOR ARRAY

(75) Inventors: Alexander Frey, Taufkirchen (DE);
Franz Hofmann, Munich (DE); Birgit Holzapfl, Munich (DE); Christian Paulus, Weilheim (DE); Meinrad Schienle, Ottobrunn (DE); Roland Thewes, Grobenzell (DE)

(73) Assignee: Siemens Aktiengesellschaft, Munich (DE)

( * ) Notice: Subject to any disclaimer, the term of this patent is extended or adjusted under 35 U.S.C. 154(b) by 1890 days.

(21) Appl. No.: 11/019,948

(22) Filed: Dec. 21, 2004

(65) Prior Publication Data

US 2005/0247559 A1 Nov. 10, 2005

Related U.S. Application Data

(63) Continuation of application No. PCT/DE03/02094, filed on Jun. 24, 2003.

(30) Foreign Application Priority Data

Jun. 24, 2002 (DE) .................................. 102 28 124
Jun. 24, 2002 (DE) .................................. 102 28 125

(51) Int. Cl.
*G01N 27/26* (2006.01)

(52) U.S. Cl.
USPC ............... 204/403.01; 435/287.1; 435/287.2; 435/6.1; 422/82.01; 422/68.1

(58) Field of Classification Search
USPC .......................... 204/403, 409, 410, 411, 412, 204/403.01–403.15, 400; 435/6, 287.2, 6.1, 435/287.1; 422/68.1, 82.01
See application file for complete search history.

(56) References Cited

U.S. PATENT DOCUMENTS 5,510,757 A * 4/1996 Kumar et al. ................. 333/104
5,828,133 A 10/1998 Caillat et al.
(Continued)

FOREIGN PATENT DOCUMENTS

DE 196 10 115 A1 9/1997
DE 199 16 92 A1 10/2000
(Continued)

OTHER PUBLICATIONS

Wang (Survey and Summary from DNA Biosensors to Gene Chips, Nucleic Acid Research, 2000, vol. 28, No. 16, pp. 3011-3016).*

(Continued)

*Primary Examiner* — Jennifer Dieterle
(74) *Attorney, Agent, or Firm* — Harness, Dickey & Pierce, P.L.C.

(57) ABSTRACT

A biosensor array having a substrate, a plurality of biosensor zones arranged on the substrate, each of which has a first terminal and a second terminal, at least one drive line and at least one detection line, the at least one drive line being electrically insulated from the at least one detection line. In each case the first terminal of each biosensor zone is coupled to precisely one of the at least one drive line and the second terminal of each biosensor zone is coupled to precisely one of the at least one detection line, and at least one of the at least one drive line and at least one of the at least one detection line is coupled to at least two of the biosensor zones. The biosensor array also has a drive unit for providing an electrical drive signal, a detection unit for detecting an electrical detection signal resulting from the electrical drive signal, and a selection unit that couples the drive unit to the drive line of a biosensor zone to be selected and the detection unit to the detection line of the biosensor zone to be selected, whereby the biosensor zone is selected.

53 Claims, 25 Drawing Sheets

(56) References Cited

U.S. PATENT DOCUMENTS

| | | | |
|---|---|---|---|
| 6,154,580 A | * | 11/2000 | Kuriyama et al. ............ 382/312 |
| 7,208,077 B1 | * | 4/2007 | Albers et al. ................. 205/782 |
| 2001/0026778 A1 | | 10/2001 | Ackley et al. |
| 2002/0028441 A1 | | 3/2002 | Hintsche et al. |
| 2002/0039743 A1 | * | 4/2002 | Hashimoto et al. ............... 435/6 |
| 2002/0093848 A1 | * | 7/2002 | Thewes et al. ................ 365/158 |
| 2003/0155942 A1 | * | 8/2003 | Thewes .......................... 324/769 |
| 2003/0186263 A1 | | 10/2003 | Frey et al. |
| 2004/0041717 A1 | * | 3/2004 | Frey et al. ....................... 341/50 |

FOREIGN PATENT DOCUMENTS

| | | | |
|---|---|---|---|
| JP | 5-281181 A | | 10/1993 |
| JP | 2003-274945 A | | 9/2003 |
| WO | WO-88/09499 A1 | | 12/1988 |
| WO | WO-93/22678 A2 | | 11/1993 |
| WO | WO-96/07917 A1 | | 3/1996 |
| WO | WO-97/21094 A1 | | 6/1997 |
| WO | WO 00/60601 | * | 10/2000 |
| WO | WO-00/62047-1 | | 10/2000 |
| WO | WO 00/62048 | * | 10/2000 |
| WO | WO-00/62048 A2 | | 10/2000 |
| WO | WO-01/43870 A2 | | 6/2001 |
| WO | WO-01/75151 A2 | | 10/2001 |
| WO | WO-01/75437 A1 | | 10/2001 |
| WO | WO 01/75462 | * | 10/2001 |

OTHER PUBLICATIONS

H. Frebel, et al., "Multianalyte sensor for the simultaneous determination of glucose, L-lactate and uric acid based on a microelectrode array", Sensors and Actuators B, 1997, vol. 43, No. 1-3, pp. 87-93.

Rainer Hintsche, et al., "Multiplexing of Microelectrode Arrays in Voltammetric Measurements", Electroanalysis, 2000, vol. 12, No. 9, pp. 660-665.

Rainer Hintsche, et al., "Microbiosensors using electrodes made in Si-technology", Frontiers in Biosensorics, Fundamental Aspects, 1997, pp. 267-283.

Peter Van Gerwen, et al., "Nanoscaled Interdigitated Electrode Arrays for Biochemical Sensors", Transducers '97, 1997 International Conference on Solid-State Sensors and Actuators, Jun. 18-19, 1997, pp. 907-910.

Christoph Hagleitner, et al., "A Gas Detection System on a Single CMOS Chip Comprising Capacitive, Calorimetric, and Mass-Sensitive Microsensors", 2002 IEE International Solid-State Circuits Conference, 26.3.

Roland Thewes, et al., "Sensor Arrays for Fully-Electronic DNA Detection on CMOS", 2002 IEEE International Solid-State Circuits Conference, 21.2.

Rainer Hintsche, et al., "Microelectrode arrays and application to biosensing devices", Biosensors & Bioelectronics, 1994, vol. 9, pp. 697-705.

Manfred Paeschke, et al., "Highly sensitive electrochemical microsensors using submicrometer electrode assays", Sensors and Actuators B, 1995, pp. 394-397.

* cited by examiner

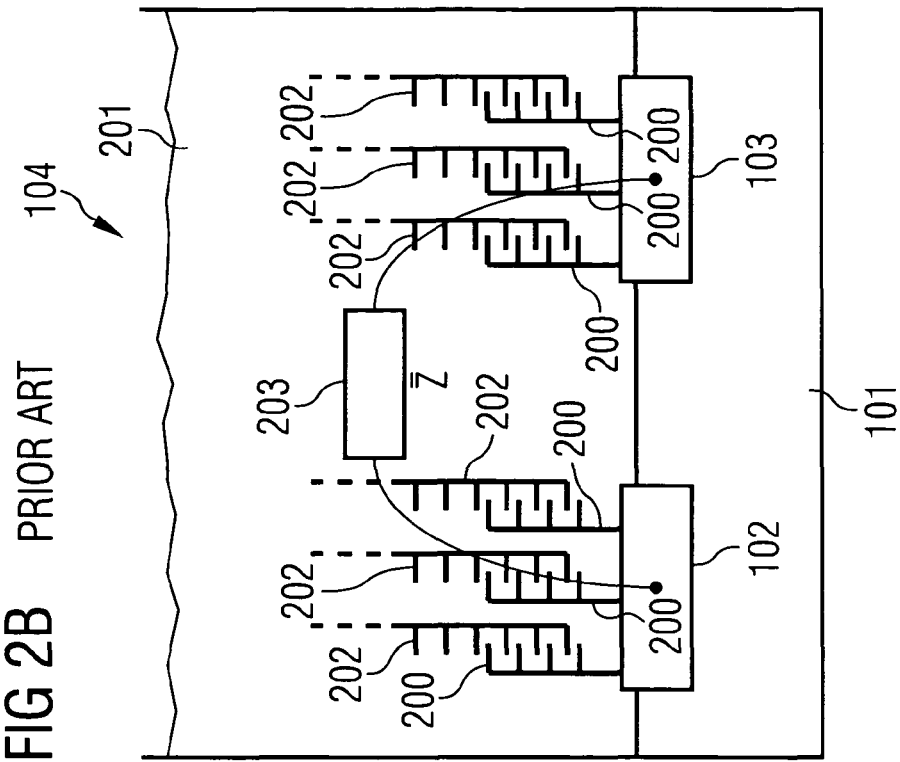
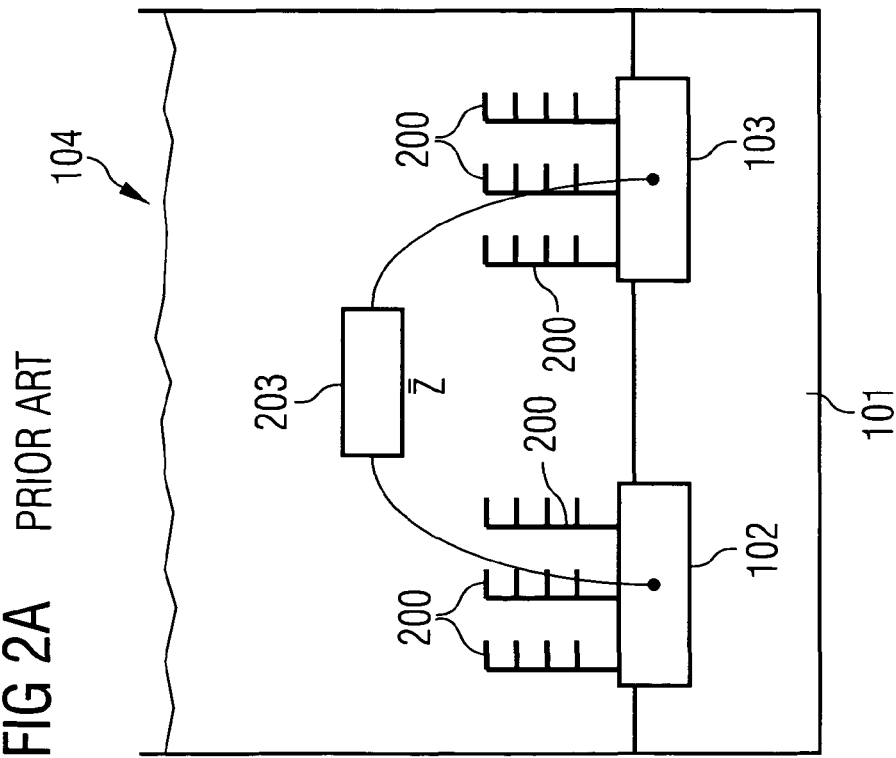

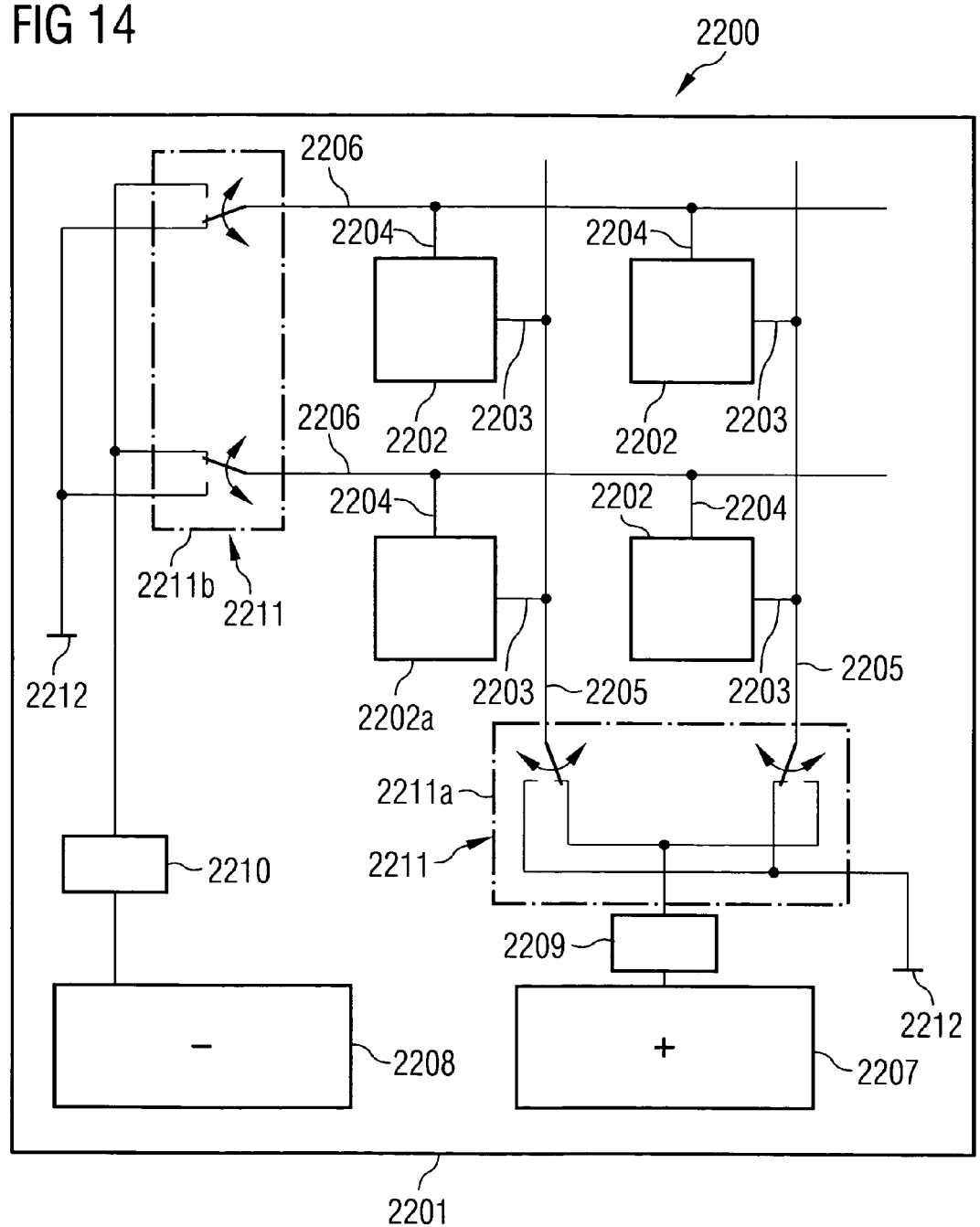

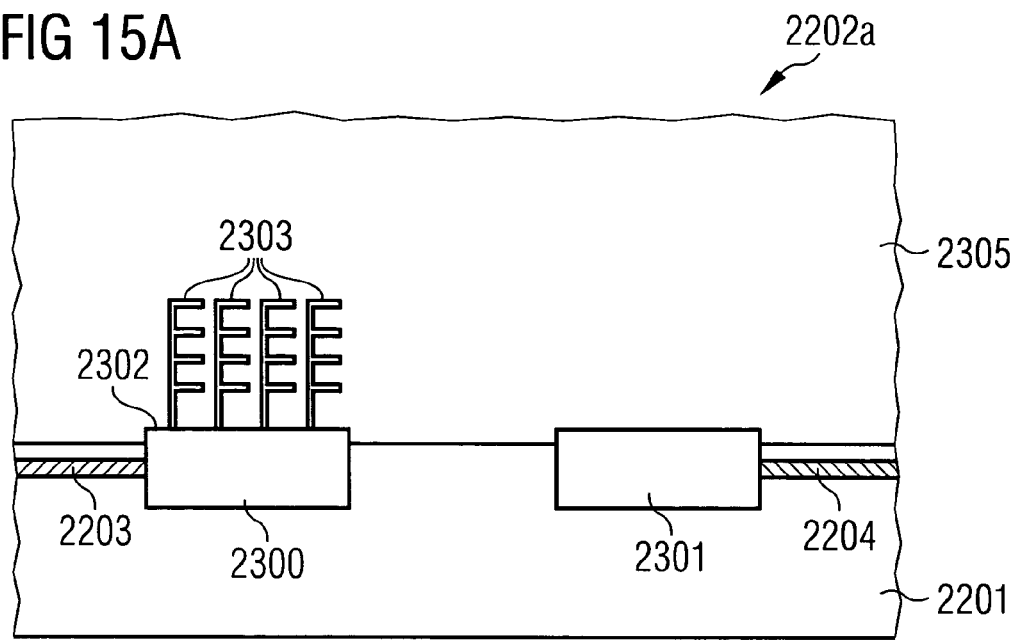
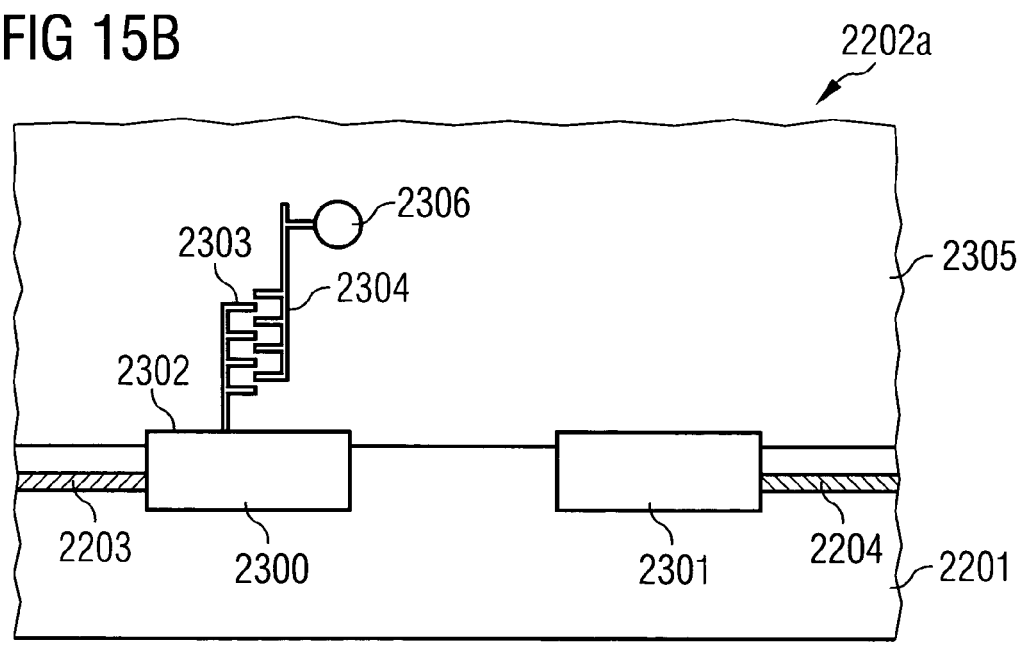

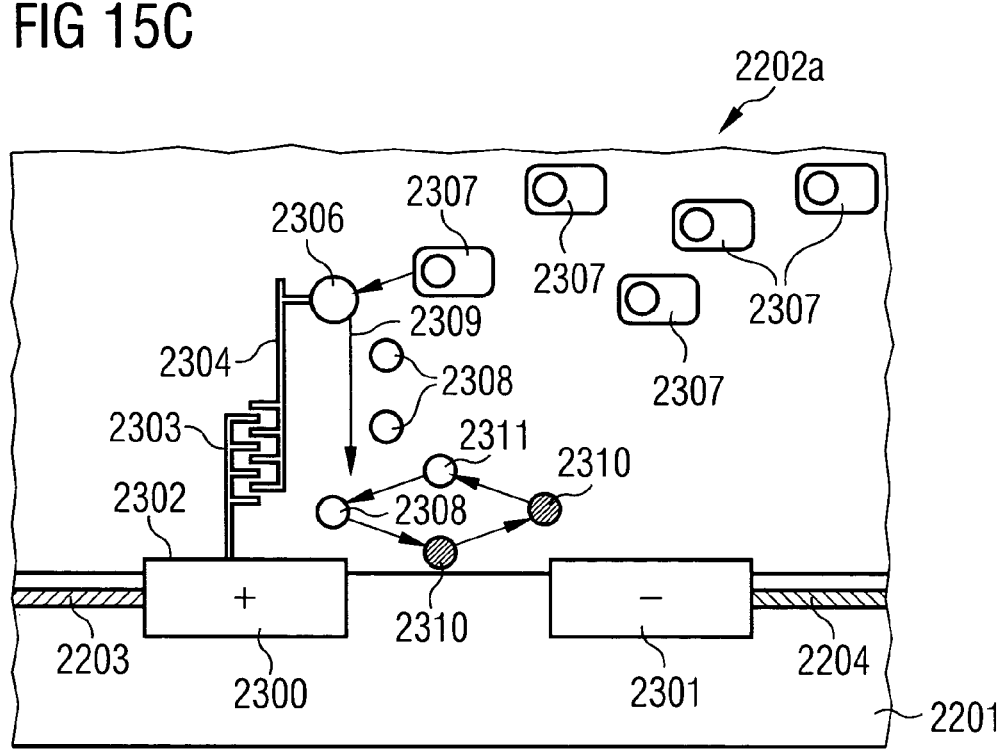

BIOSENSORS ARRAY AND METHOD FOR OPERATING A BIOSENSOR ARRAY

CROSS-REFERENCE TO RELATED APPLICATION

This application is a continuation of International Patent Application Serial No. PCT/DE2003/002094, filed Jun. 24, 2003, which published in German on Dec. 31, 2003 as WO 2004/001405 A1.

FIELD OF THE INVENTION

The invention relates to a biosensor array and a method for operating a biosensor array.

BACKGROUND OF THE INVENTION

Two-pole impedance sensors have been proposed for various fields of sensor technology. Such two-pole impedance sensors are described in WO 93/22678, DE 19610115 A1, U.S. Patent Ser. No. 60/007840, and Peter Van Gerwen et al., "Nanoscaled Interdigitated Electrode Arrays for Biochemical Sensors", Proc. International Conference on Solid-State Sensors and Actuators (Transducers '97), pp. 907-910, 1997, for the area of biosensor technology, and Hagleitner, C. et al. "A Gas Detection System on a Single CMOS-Chip comprising capacity, calorimetric, and mass sensitive microsensors", Proc. International Solid-State Circuit Conference (ISSCC), p. 430, 2002, proposes a two-pole impedance measurement for the sensor technology of other chemical substances, for example gas sensors.

A description is given below, referring to FIG. 1A to FIG. 5B, of a sensor arrangement in accordance with the prior art which represents a DNA sensor on the basis of the two-pole impedance method.

FIG. 1A, FIG. 1B show an interdigital electrode arrangement 100, in which a first electrode structure 102 and a second electrode structure 103 are applied in a substrate 101, said electrode structures clearly being interdigitated. FIG. 1A shows a plan view of the interdigital electrode arrangement 100, and FIG. 1B shows a cross-sectional view along the section line I-I' shown in FIG. 1A. The interdigital electrode arrangement 100 contains periodic electrode components of the electrode structures 102, 103 arranged next to one another.

The structure shown in FIG. 1A, FIG. 1B comprises electrodes arranged periodically next to one another, so-called interdigital electrodes.

In order to explain the principle of the functioning of the interdigital electrode arrangement 100, a first partial region 104 of the interdigital electrode arrangement 100 is described with reference to FIG. 2A, FIG. 2B.

The first partial region 104 is shown as a cross-sectional view in a first operating state in FIG. 2A, and as a cross-sectional view in a second operating state in FIG. 2B.

Capture molecules 200 (DNA half strands) are in each case immobilized on the electrode structures 102, 103. Gold material is preferably used for the electrode structures 102, 103, so that the immobilization of the capture molecules 200 is realized using the particularly advantageous gold-sulfur coupling known from biochemistry, by virtue of, by way of example, a thiol group (SH group) of the capture molecules 200 being chemically coupled to the gold electrodes 102, 103.

Situated above the sensor electrodes 102, 103 during active sensor operation is an electrolytic analyte 201 to be examined, which is intended to be examined for the presence of particles 202 to be detected (for example specific DNA molecules). A hybridization, that is to say a binding of DNA strands 202 to the capture molecules 200, is effected only when the capture molecules 200 and the DNA strands 202 match one another in accordance with the key-lock principle (cf. FIG. 2B). If this is not the case, then hybridization is not effected (not shown). The specificity of the sensor is thus derived from the specificity of the capture molecules 200.

The electrical parameter evaluated during this measurement is the impedance $\overline{Z}$ 203 between the electrodes 102, 103, which is illustrated schematically in FIG. 2A, FIG. 2B. On account of a hybridization that has taken place, the value of the impedance changes since the DNA particles 202 to be detected and the capture molecules 200 are composed of a material which has electrical properties deviating from those of the material of the electrolyte, and, after the hybridization, the electrolyte is clearly displaced from the volume region surrounding the electrodes 102, 103.

FIG. 3 shows a second partial region 105 (cf FIG. 1B) of the interdigital electrode arrangement 100 in a cross-sectional view.

The second partial region 105 represents a larger partial region of the interdigital electrode arrangement 100 than the first partial region 104 illustrated in FIG. 2A, FIG. 2B. FIG. 5 schematically shows the profile of the electric field lines 300 between respectively adjacent electrode structures 102, 103. As is furthermore shown in FIG. 3, the field profiles are periodic within a respective region imagined by virtue of two lines of symmetry 501, with the result that the consideration of two directly adjacent electrode structures 102, 103 as shown in FIG. 2A, FIG. 2B is sufficient. Furthermore, a coverage region 302 is shown schematically in FIG. 3 for each of said electrode structures 102, 103, said coverage region representing the capture molecules 200 immobilized on the electrode structures 102, 103 and particles 202 to be detected that have possibly hybridized with said capture molecules. It can clearly be understood from the illustration shown in FIG. 3 that the profile of the field lines 300 is significantly influenced on account of a hybridization event since the physical-chemical properties of, in particular, the coverage region 302 are altered.

It should furthermore be noted that capture molecules may supplementarily or alternatively be provided in regions between electrodes 102, 103 (not shown). The electrical properties of the electrolyte once again change in the case of hybridization events between particles to be detected and capture molecules provided in regions between the electrodes.

FIG. 4 schematically shows a simplified equivalent circuit diagram 400 of the first partial region 104 of the interdigital electrode arrangement 100 as shown in FIG. 2A. The equivalent circuit diagram 400 shows a variable first capacitance 401 $C_M$, the value of which is dependent on the extent of a hybridization that has taken place at the electrode structure 102. A variable first nonreactive resistance 402 $R_M$ is connected in parallel therewith. The components 401, 402 clearly represent the electrical properties of the region surrounding the first electrode structure 102. Furthermore, a variable second capacitance 403 $C_E$ and a variable second nonreactive resistance 404 $R_E$ connected in parallel therewith are shown, which represent the electrical properties of the analyte 401. Also shown are a variable third capacitance 405 $C_M$ and a variable third nonreactive resistance 406 $R_M$ connected in parallel therewith, representing the electrical properties of the region surrounding the second electrode structure 103. As is furthermore shown in FIG. 4, the parallel circuit comprising components 401, 402, the parallel circuit comprising components 403, 404 and the parallel circuit comprising components 405, 406 are connected in series. The components 401 to 406 are represented as variable in order to illustrate that their values may change on account of a sensor event.

As is shown in the equivalent circuit diagram 500 of the first partial region 104 as shown in FIG. 5A, an AC voltage V is applied to one of the electrodes 102, 103 in order to determine the value of the impedance. The AC voltage V is provided using an AC voltage source 502. The AC current I flowing through the arrangement is detected using the ammeter 501. The components 501, 502 are connected in series with one another and are connected between the parallel circuit comprising components 405, 406 and the electrical ground potential 503. The AC current signal I resulting at the electrodes 102, 103 is evaluated together with the applied AC voltage V in order to determine the impedance. As an alternative, a signal, that is to say an electrical voltage, may in each case also be applied to both electrodes 102, 103; the signals are then in antiphase.

The version of a simplified equivalent circuit diagram 510 as shown in FIG. 5B differs from the equivalent circuit diagram 500 shown in FIG. 5A in that the elements $C_M$ 401, 405 and $R_M$ 402, 406 are combined to form a first effective capacitance $2C_M$ 511 and, respectively, to form a first effective nonreactive resistance 512 $2R_M$.

The distance between the electrodes 102, 103 typically lies in the sub-μm range. In accordance with the interdigital electrode arrangement 100, a multiplicity of electrode components (clearly fingers) of the electrode structures 102 and 103 are arranged parallel. Circular arrangements can be used for reasons of fluidics, as is described in R. Thewes et al., "Sensor Arrays for Fully Electronic DNA Detection on CMOS", Proc. Int. Solid-State Circuits Conf. (ISSCC), p. 350, 2002, for a different detection method based on the use of interdigital electrodes. The external dimensions or the diameter of such individual sensors is in the region of approximately 100 μm or even less down into the single-digit mm range.

With regard to the exciting AC voltage V, it should be taken into consideration that its root-mean square value or its peak value is not to exceed a specific maximum value. The biochemical or electrochemical boundary conditions that enable the operation of such sensors are violated when such a maximum value is exceeded. If the electrode potential (which is referred to the electrical potential of the electrolyte) exceeds an upper threshold value, then specific substances in a region surrounding an electrode may be oxidized. If the electrical potential (which is referred to the electrical potential of the electrolyte) falls below a lower threshold value, substances are reduced there. An undesirable oxidation or reduction may have the effect, inter alia, that the chemical bonds entered into in the course of immobilization and hybridization are broken. Furthermore, electrolysis may commence at the sensor electrodes, with the result that the electrolysis products bring the chemical milieu required for operation of the sensors out of the required equilibrium and lead to gas formation. The absolute values of the critical potentials depend on the composition and the concentration ratio of the chemical surroundings of the electrodes (for example immobilization layer, analyte, etc.).

Typical values for the exciting voltage lie in the range of a few 10 mV to at most in the region around 100 mV. This is an important boundary condition for the operation of such sensors since the resulting measurement signal (current intensity I), with regard to its magnitude, is approximately directly proportional to the applied voltage.

There is often an interest in carrying out not just one test on a sensor arrangement but many tests on a suitable sample, the analyte, temporally in parallel. Miniaturized bio-/chemosensor arrays that can be realized on corresponding chips serve for parallel detection of different molecules or different substances in an analyte to be examined. A large number of the corresponding electrical sensors are realized on a glass, plastic, silicon or other substrate. On account of the property of parallelization, such sensor array chips including a corresponding evaluation system are afforded diverse applications in medical diagnosis technology, in the pharmacological industry (for example in the area of pharmacological screening, "high throughput screening", HTS), in the chemical industry, in foodstuffs analysis, in ecological and foodstuffs technology and analysis, etc.

However, impedance sensors (such as the one described with reference to FIG. 1A to FIG. 5B) have hitherto been presented only as individual sensors or in small arrays, in principle comprising a stringing together of individual sensors.

In order to be able to carry out a large number of tests on an analyte temporally in parallel, it is endeavored to arrange a larger number of such sensors specified with respect to different substances in an array on a chip. Realizing arrays with two-pole impedance sensors gives rise to the challenge that the signals of all the sensors have to be fed to a read-out device. If e.g. a passive chip with 8×12=96, 32×48=1536 or generally m×n positions is present, 2×96=192, 2×1536=3072 or 2×m×n individual pads are present. Each sensor has to be separately readable, and the number of chip pads used is not to be too high on account of the production outlay for chip and reader and primarily for reasons of security in contact-connection (signal integrity). The simple approach, e.g. connecting all pads to the reader, yields 2×m×n (that is to say, in the example, 192 or 3052) pads. This is considerably too large for practical applications. This similarly holds true for the approach of operating one electrode in a common fashion and connecting all the remaining electrode terminals and also the common electrode to the reader. In this case, the number of pads is admittedly lower (n×m+1, that is to say 97 or 1537 in the examples), but is still very large.

One possibility is to use so-called active chips which, apart from the materials for the transducers (in particular the sensor electrodes, e.g. gold for the interdigital electrodes), provide additional active circuits for the signal preprocessing and the multiplexing of signals on-chip and also corresponding wiring planes. A solution of this type is described in R. Thewes et al. for a different method that is likewise based on the use of interdigital electrodes.

The prior art discloses biosensors that operate in accordance with the principle of redox recycling (cf. R. Hintsche et al, "Microelectrode arrays and application to biosensing devices", Biosensors & Bioelectronics, pp. 697-705, 1994, R. Hintsche et al., "Microbiosensors using electrodes made in Si-technology" in "Frontiers in Biosensorics I", F. Scheller et al. ed., Birkhauser, Basel, Switzerland, 1997, M. Paeschke et at, "Highly sensitive electrochemical microsensors using submicrometer electrode arrays", Sensor and Actuators B, pp. 394-397, 1995, and WO 00/62048).

FIG. 1C, which illustrates an interdigital electrode arrangement as in FIG. 1A, FIG. 1B, shows a redox recycling biosensor 110 in accordance with the prior art.

Such a redox recycling sensor 110 requires a four-electrode system formed on a substrate 111. The redox recycling biosensor 110 has a first interdigital electrode 112 and a second interdigital electrode 113 that is clearly intermeshed with the latter in a finger-type fashion. Typical values for the width of and the distance between the interdigital electrodes 112, 113 lie in the range of between approximately 0.5 μm and approximately 2 μm.

Capture molecules (not shown) are immobilized on the interdigital electrodes 112, 113, and can hybridize with particles to be detected in a solution to be examined. In accordance with the redox recycling principle, during operation of the redox recycling biosensor 110, oxidation and reduction processes of electrochemically activated particles are effected in the case of a sensor event at the interdigital electrodes 112, 113. By means of a label molecule that is chemically bound to particles of an analyte that are to be detected and have hybridized with capture molecules, electrochemically activated particles are produced if a special component is added to the solution.

The further electrodes shown in FIG. 1, namely a reference electrode 114 and a counterelectrode 115, form, together with a differential amplifier 116, a potentiostat. A noninverting input 116a of the differential amplifier 116 is coupled to the electrical ground potential 117, whereas an inverting input 116b of the differential amplifier 116 is coupled to the reference electrode 114. An output 116c of the differential amplifier 116 is coupled to the counterelectrode 115. The electrochemical potential of an electrolyte introduced into the redox recycling biosensor 110 is measured by means of the reference electrode 114. By means of the counterelectrode 115, the differential amplifier 116 is regulated as a regulating amplifier to a predetermined electrical potential. It should be noted that the predetermined potential is clearly the electrical potential at the noninverting input 116a of the differential amplifier 116, the electrical ground potential 117 in accordance with the example shown.

For the operation of the redox recycling biosensor 110, electrical voltages having a different sign relative to the reference potential (ground potential 117) are applied to the interdigital electrodes 112, 113, which are operated as generator and collector electrodes, by means of a first DC voltage source 118 and by means of a second DC voltage source 119. The magnitude of said voltages is to be chosen to be high enough that the processes of oxidation and reduction of the redox recycling substance function reliably and efficiently, but on the other hand they are not to be chosen too high in order to avoid unintended electrochemical processes (e.g. electrolysis) at the electrodes 112, 113.

It should be noted that very precise threshold values for the commencement of oxidation and reduction of specific substances do not exist. In practice, values are chosen whose magnitude in each case lies sufficiently reliably (typically a few 10 mV) above these threshold ranges. In practice, the applied voltages lie in the region of a few 100 mV (for example +300 mV and −100 mV) for the substances used in R. Thewes et al.

As is furthermore shown in FIG. 1C, a first ammeter 120 coupled to the first DC voltage source 118 and a second ammeter 121 coupled to the second DC voltage source 119 are provided. The first ammeter 120 can be used to detect an electric current resulting from the applied voltages and the reduction/oxidation processes at the second interdigital electrode 113. The second ammeter 121 can be used to detect an electric current resulting from the applied voltages and the reduction/oxidation processes at the first interdigital electrode 112. The values of said currents are a characteristic measure of the sensor events that have taken place at the electrodes 112, 113 and thus of the concentration of particles to be detected in a solution to be examined.

Electrochemical sensors known from the prior art, such as the redox recycling biosensor 110, have hitherto been presented only as individual sensors in small "passive" arrays, clearly as a stringing together of a few individual sensors, or in "active" arrays which, apart from the actual biosensors, contain further active components on which either switching matrices, cf. WO 00/62048, or complex circuit technology, cf. R. Thewes et al., are or is contained.

For many applications, it is desirable to carry out not just one test with a biosensor but many tests in a given sample, the analyte, temporally in parallel. Miniaturized bio-/chemosensor arrays that can be realized on corresponding chips serve for the temporally parallel detection of different particles to be detected in an analyte to be examined. A large number of the corresponding sensors can be realized on a substrate, for example on a glass, plastic, silicon or other substrate. On account of the high degree of parallelization, such sensor arrangements including a corresponding evaluation system are afforded diverse applications in medical diagnosis technology, in the pharmacological industry (e.g. for pharmacological screening, "high throughput screening", HTS), in the chemical industry in foodstuffs analysis, in ecological and foodstuffs technology and analysis.

Realizing passive arrays with sensors in accordance with the principle of redox recycling gives rise to the challenge that the signals of all the sensors have to be fed to a read-out device. If, by way of example, a passive substrate with 8×12=96, 32×48=1536 or generally in the case of a matrix-type arrangement with m rows and n columns m×n positions is present, this requires 2×96=192, 2×1536=3072 or generally 2 m×n separate electrode terminals of the sensors and also two further terminals for the reference electrode and counterelectrode of the potentiostat arrangement. Each biosensor zone should be separately readable, and the number of chip terminals ("pads") used is not to be too high for reasons of the outlay (for chip and read-out device) and primarily for reasons of security in contact-connection (signal integrity).

A simple approach, for example coupling all the electrode terminals to the read-out device, yields 2 m×n+2, that is to say, in the example, 194 or 3074, terminals and therefore cannot be realized or cannot be realized satisfactorily. This similarly holds true for the approach of operating one electrode of all the sensor zones in a common fashion and coupling all the remaining electrode terminals and also the common electrode to the read-out device. In this case, the number of terminals is admittedly lower, namely n×m+1+2 (99 or 1539 in the example), but still much too large.

The disadvantage of the approaches described in WO 00/62048, R. Thewes et al., which make use of active arrays with a complicated CMOS technology for the individual sensor zones, consists in the high manufacturing costs compared with purely passive arrays in which CMOS circuits are obviated for the sensor zones.

WO 96/07917 discloses a self-addressable, self-assembling microelectronic system for carrying out molecular diagnosis, analysis, multiple step and multiplex reactions in microscopic formats.

WO 01/43870 A2 discloses a method and an apparatus which have a platform for a column- and row-addressable high-density biosensor arrangement.

WO 01/75151 A2 discloses a method for detecting macromolecular biopolymers by means of an electrode arrangement.

WO 88/09499 A1 discloses an optimized capacitive sensor for chemical analysis and measurement.

SUMMARY OF THE INVENTION

The invention is based on the problem of providing a biosensor array in which it is possible, with a tenable production outlay, to read out sensor signals from an arrangement of sufficiently many biosensor zones.

The problem is solved in accordance with one aspect of the invention by means of a biosensor array and by means of a method for operating a biosensor array.

In accordance with one aspect of the invention, the biosensor array according to the invention contains a substrate and a plurality of biosensor zones arranged on the substrate, each of which biosensor zones has a first and a second terminal. Furthermore, the sensor arrangement has at least one drive line and at least one detection line, the at least one drive line being electrically insulated from the at least one detection line. In other words, each drive line is electrically decoupled from each detection line in a crossover region. The respective first terminal of each biosensor zone is coupled to precisely one of the at least one drive line, and the respective second terminal of each biosensor zone is coupled to precisely one of the at least one detection line. At least one of the at least one drive line and at least one of the at least one detection line are coupled to at least two of the biosensor zones. Furthermore, the biosensor array contains a drive unit for providing an electrical drive signal, a detection unit for detecting an electrical detection signal resulting from the electrical drive signal, and a selection unit set up in such a way that it couples the drive unit to the drive line of a biosensor zone to be selected and the detection unit to the detection line of the biosensor zone to be selected, whereby the biosensor zone is selected.

Furthermore, said one aspect of the invention provides a method for operating a biosensor array having the features mentioned above. In accordance with the method, the drive unit is coupled to the drive line of a biosensor zone to be selected and the detection unit is coupled to the detection line of the biosensor zone to be selected, whereby the biosensor zone is selected. Furthermore, the drive line of the at least one selected biosensor zone is provided with an electrical drive signal. Moreover, an electrical detection signal of the selected biosensor zone that results from the electrical drive signal is detected on the detection line of the at least one selected biosensor zone.

BRIEF DESCRIPTION OF THE DRAWINGS

Exemplary embodiments of the invention are illustrated in the figures and are explained in more detail below.

In the figures:

FIGS. 2A, 2B show cross-sectional views of a first partial region of the interdigital electrode arrangement shown in FIG. 1 at different points in time during a method for operating the interdigital electrode arrangement in accordance with the prior art;

FIG. 14 shows a sensor array in accordance with a sixth exemplary embodiment of the invention;

FIG. 15A to FIG. 15C show cross-sectional views of a redox recycling biosensor zone of the biosensor array shown in FIG. 14 in different operating states;

DETAILED DESCRIPTION OF PREFERRED EMBODIMENTS OF THE INVENTION

Figure 1A:
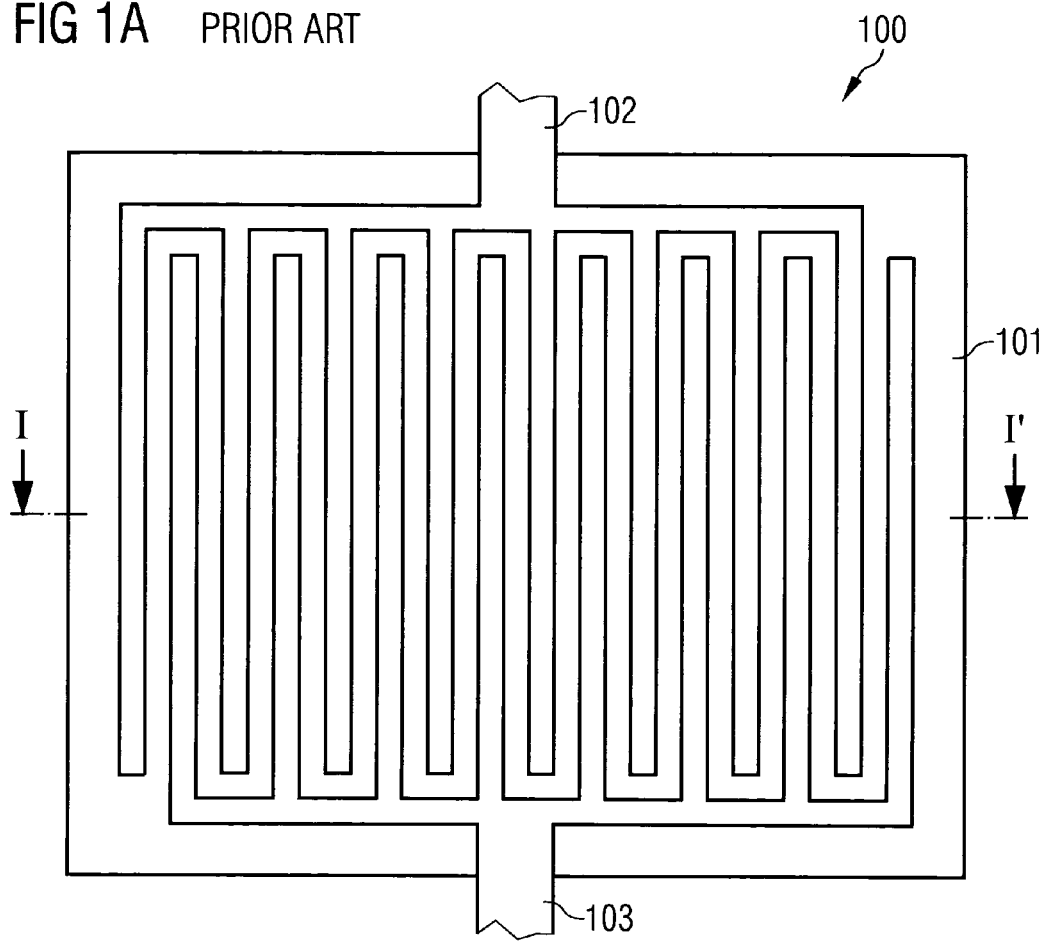
FIGS. 1A, 1B show a plan view and a cross-sectional view along the section line I-I' of an interdigital electrode arrangement in accordance with the prior art.
Figure 1B:
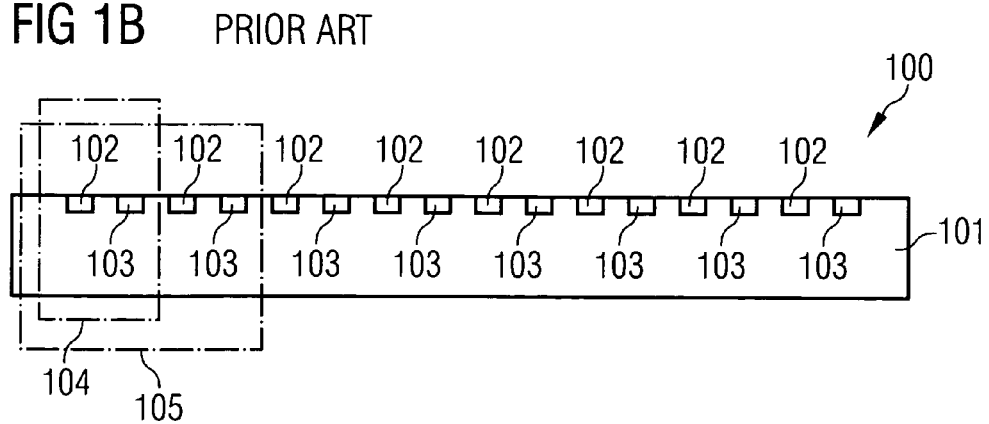
Figure 1C:
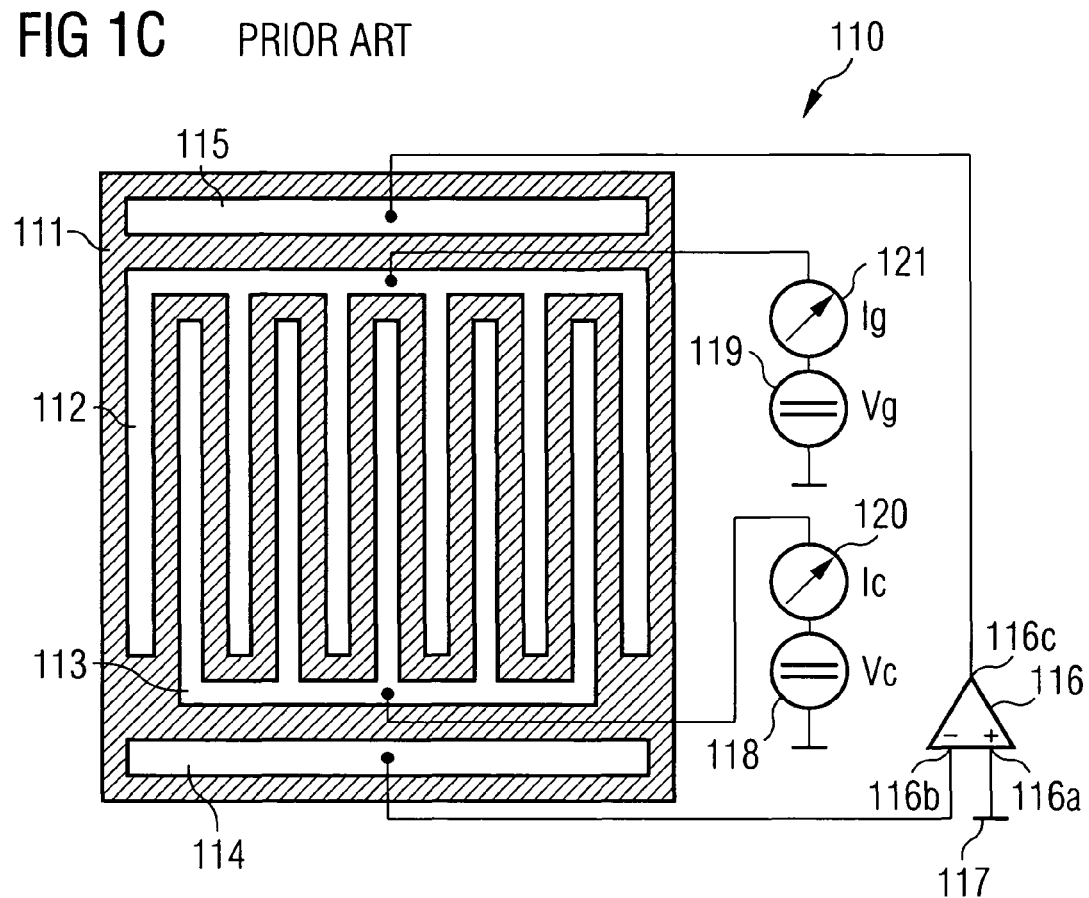
FIG. 1C shows another interdigital electrode arrangement in accordance with the prior art.
Figure 3:
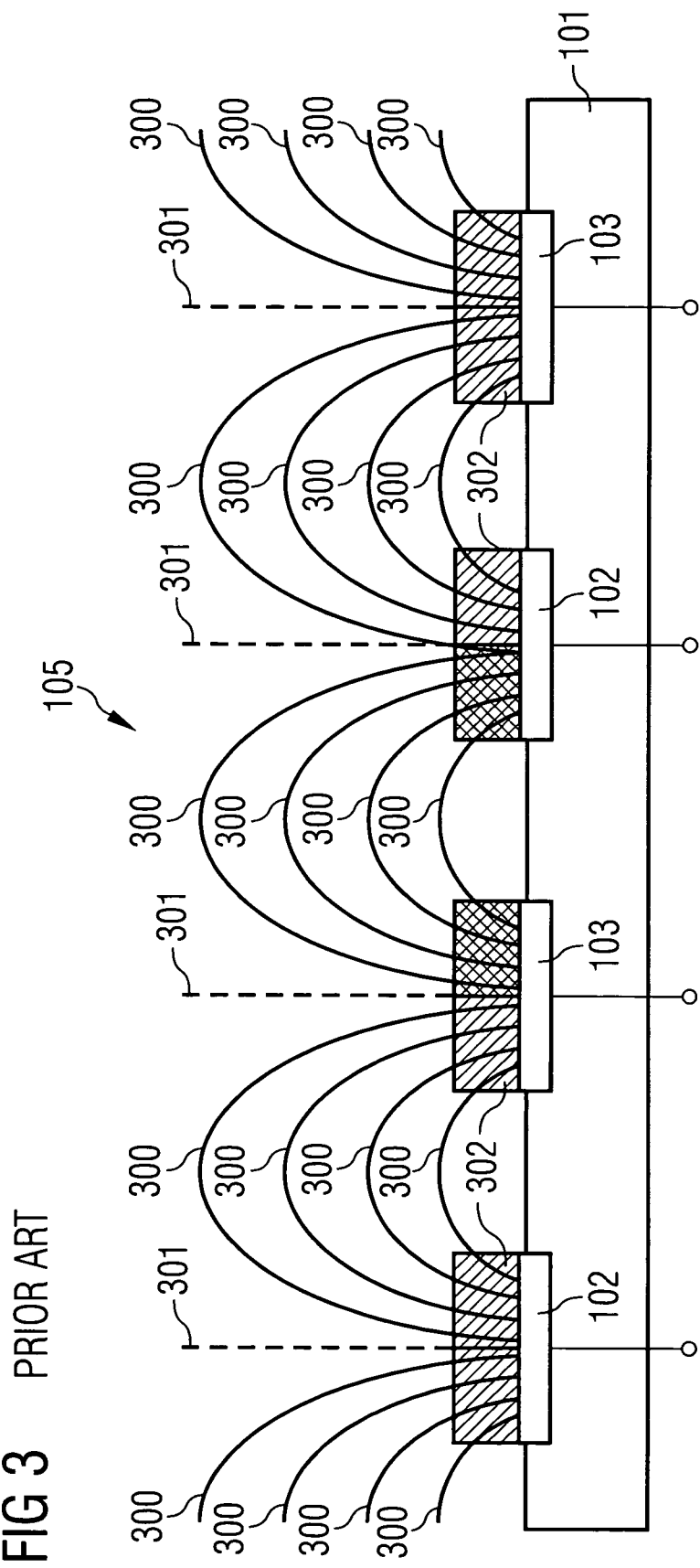
FIG. 3 shows a cross-sectional view of a second partial region of the interdigital electrode arrangement in accordance with the prior art as shown in FIG. 1.
Figure 4:
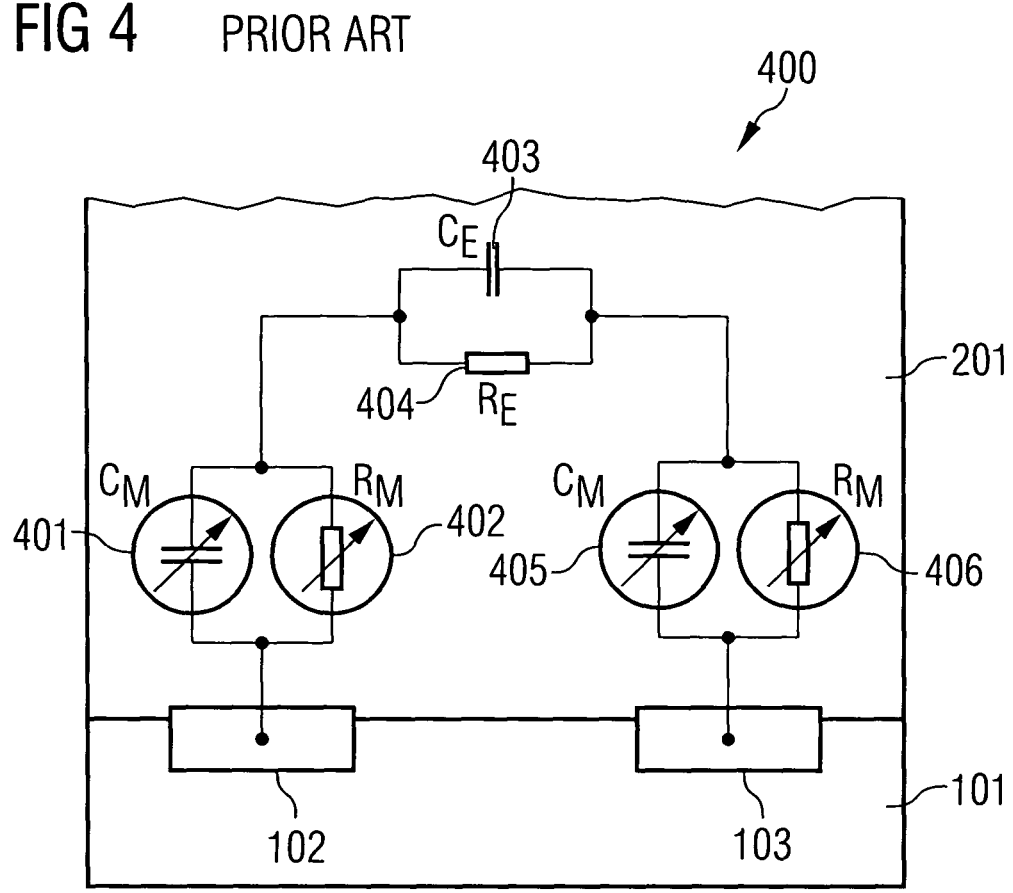
FIG. 4 shows an equivalent circuit diagram of the first partial region of the interdigital electrode arrangement from FIG. 1 in accordance with the prior art.

A basic idea of the invention consists in providing drive lines and detection lines that are provided jointly for in each case a plurality of biosensor zones of a biosensor array, thereby considerably reducing the number of signal lines required for operating the biosensor array. This makes it possible to operate a biosensor array (in particular on a passive chip) with a relatively small number of signal lines and a small number of pads coupled to the signal lines. This saves space on the biosensor array, which enables a higher integration density, and the production costs are reduced. The array architecture according to the invention is also of interest for active chips since it permits the circuitry outlay per biosensor zone to be kept low, which in turn enables the production of high-density arrays. In the case of active biosensor arrays, additional circuit devices (for example preamplifiers, AD converters, etc.) are provided on the substrate.

For a, by way of example, matrix-type arrangement of the biosensor zones along detection lines provided as row lines and along drive lines provided as column lines, it is possible for e.g. m columns to be optionally coupled to an exciting voltage source of the drive unit or to electrical ground potential. The n rows may optionally be coupled to a current detecting device of the detection unit or to the electrical ground potential. The selection of the coupling of the terminals of the biosensor zones to the voltage source or the ground potential and to the current detecting device or the electrical ground potential is effected by means of the selection unit.

By way of example, an electrical voltage may be applied as electrical drive signal to precisely one column line, and the current detecting unit for detecting the electrical detection signal resulting from the electrical drive signal may be coupled to precisely one row line. An electric current then flows from the voltage source into each biosensor zone of the selected column. However, only the electric current that flows into the biosensor zone of the selected row is measured in the current detecting unit. With the m drive lines and n detection lines, essentially only n+m signal lines and thus pads are required for the biosensor array according to the invention. Therefore, only twenty signal lines and pads are required for a biosensor array with 8×12=96 positions, and eighty signal lines and pads are required for a chip with 32×48=1532 positions. The optimum ratio of the number of pads relative to the number of biosensor zones results for a matrix-type arrangement where n=m, that is to say for a biosensor array with a square architecture (number of rows=number of columns).

The invention clearly makes it possible to significantly reduce the production-technological outlay for a biosensor array by virtue of the fact that at least one of the at least one drive line and at least one of the at least one detection lines is coupled to at least two of the biosensor zones. In other words, provision is made of signal lines for driving and detection that are common to a respective plurality of biosensor zones.

The biosensor zones preferably contain two electrodes (e.g. two interdigital electrodes), each of which is coupled to one of the terminals of the biosensor zone.

The biosensor array according to the invention may have an evaluation unit set up in such a way that it determines for the at least one selected biosensor zone on the basis of the value of the drive signal and the detection signal whether sensor events have taken place at the at least one selected biosensor zone and/or the quantity in which sensor events have taken place at the at least one selected biosensor zone. By way of example, if the biosensor zones can be operated using the impedance method described above with reference to FIG. 1A to FIG. 5B, using an interdigital electrode arrangement, then the drive signal may be an electrical AC voltage and the detection signal may be an AC current that flows through a selected biosensor zone and results from the AC voltage. The value of the impedance of the biosensor zone can then be determined from the drive signal and the detection signal. Since the value of the impedance differs before and after a hybridization event that has taken place, when the value of the impedance changes, it is possible to draw a conclusion about whether a sensor event has taken place at the selected biosensor zone and/or the quantity in which sensor events have taken place there. As a result, it is possible to determine whether an analyte to be examined contains particles to be detected, and, if appropriate, the concentration in which the particles to be detected are contained in the analyte. The evaluation unit may be provided in a manner integrated on the substrate or externally with respect to the substrate.

The at least one biosensor zone may be an electrochemical biosensor zone or an impedance biosensor zone. If the biosensor zone is an electrochemical biosensor zone, it may be set up as a redox recycling biosensor zone, in particular. In the case of a redox recycling biosensor zone, particles to be detected are provided with an enzyme label which, after a hybridization event has taken place with capture molecules immobilized on the sensor zone, is used for cleaving an electrochemically inactive substance to be introduced into the arrangement into two partial molecules, at least one of which is electrochemically active. This leads to an alteration of the electrical properties of the respective sensor position of the biosensor array.

The at least one biosensor zone is preferably set up as an interdigital electrode biosensor zone. In other words, it may be configured and operable like the interdigital electrode arrangement 100 described with reference to FIG. 1A to FIG. 5D.

The biosensor zones may be grouped to form a plurality of biosensor groups in such a way that each biosensor group can optionally be operated separately from the other biosensor groups or jointly with at least a portion of the other biosensor groups. A compartmentalization of the biosensor array is clearly possible. By way of example, if a partial region of the biosensor zones is sufficient for a specific application and the other biosensor zones are not required for this application, then the biosensor zones of the partial region may be grouped to form a group and this group may be operated separated from the rest of the biosensor zones.

The substrate may be a ceramic substrate, a semiconductor substrate (in particular a silicon substrate, that is to say a silicon wafer or a silicon chip), a glass substrate or a plastic substrate.

The electrical drive signal is preferably a temporally variable electrical signal. A temporally variable electrical signal is advantageous particularly when an impedance to be detected is dominated by a capacitive component.

The drive signal may be a temporally variable electrical voltage, and the read-out signal may be a temporally variable electric current. As an alternative, the drive signal may be a temporally variable electric current and the read-out signal may be a temporally variable electrical voltage.

The time dependence of the electrical drive signal may be, in particular, a mathematical sine function, a rectangular function, a sawtooth function, a triangular function or a step function.

It is advantageous to configure the biosensor array according to the invention as an active sensor chip that may contain integrated circuits having any desired functions. An analog-to-digital converter circuit may be integrated in the substrate of the biosensor array, which circuit is set up in such a way that it converts an analog electrical signal into a digital signal and provides it to the evaluation unit. Furthermore, an electrical supply unit may be integrated in the substrate, which supply unit is set up in such a way that it provides electrical voltage signals and/or electric current signals to the drive unit and/or to the selection unit. Moreover, a digital-to-analog converter circuit may be integrated in the substrate, which circuit is set up in such a way that it converts a digital voltage signal and/or current signal of the supply unit into an analog signal and provides it to the drive unit and/or to the selection unit. It is also possible to provide an input/output interface for the connection of an external apparatus on the biosensor array. This may be set up for example as a digital I/O interface. Furthermore, an amplifier unit, set up for amplifying the electrical detection signal, may be integrated in the substrate. Amplification "on-chip" avoids the situation wherein an analog signal that is susceptible to interference runs along a large region of signal lines and is therefore exposed to interference. As a result, the signal-to-noise ratio is improved.

Preferably, the at least one drive line, on the one hand, and the at least one detection line, on the other hand, are at least partly formed in two different conductor planes (e.g. metallization planes) in and/or on and/or below the substrate. The use of two different line planes enables an electrically insulated line crossover between drive lines and detection lines. The two line planes (in particular metal planes) may be realized in the manner known from processes appertaining to microelectronics. In that case, all the metal planes are embedded in intermetal dielectrics above the bulk material (the substrate). As an alternative, however, it is also possible for one of the line planes to be realized in the same plane (and preferably from the same material) as the transducer elements themselves (e.g. gold material of interdigital electrodes). In other words, the biosensor zones may be formed in precisely one of the line planes.

Furthermore, in a first line section, in which the at least one drive line and the at least one detection line are free of a mutual crossover, the at least one drive line and the at least one detection line may be formed such that they run in the same plane. In a second line section, in which the at least one drive line and the at least one detection line mutually cross one another, the at least one drive line and the at least one detection line may be formed such that they run in different planes.

In other words, a second conductor plane need not necessarily be provided in a buried fashion with regard to a first conductor plane. It is also possible to realize both planes partly in the same plane as the transducers (and to produce them from the same material as the transducers). It is only in crossover regions between drive lines and detection lines that a bridging of the crossover region is then necessary in order to ensure an electrical insulation between drive lines and detection lines. Between the line sections running in the bridging region in different planes, it is preferable to use an electrically insulating material between the lines.

Preferably, the first line section of the at least one drive line and/or of the at least one detection line is coupled to the second line section of the at least one drive line and/or of the at least one detection line by means of at least one electrical contact-connection element arranged in a manner essentially running vertically with respect to the substrate. In particular, vias are possible in order to couple line sections of the drive lines and/or of the detection lines that run in different planes to one another.

The at least one drive line and/or the at least one detection line may be formed in a manner running on an underside of the substrate or beneath the substrate.

In other words, a line plane may be realized for example also on the underside of a chip. Plated-through holes are necessary for this purpose. Furthermore, a dielectric layer may be formed beneath the chip, electrically conductive structures being embedded in said dielectric layer in order to form signal lines.

The biosensor zones of the biosensor array according to the invention may essentially be arranged in a rectangular, preferably square, hexagonal or triangular matrix. A matrix-type rectangular arrangement of the biosensor zones with an identical number of rows and columns (square matrix) enables a particularly favorable ratio of the number of required signal lines (and pads) to the number of biosensor zones.

The drive unit may have a supply unit that is common to all the biosensor zones and is set up in such a way that it can be used to apply the electrical drive signal to the at least one selected biosensor zone.

In other words, it is possible, by way of example, to provide a single common voltage source as a supply unit which, using the functionality of the selection unit, is coupled to in each case a biosensor zone or a portion of the biosensor zones (for example a column of biosensor zones) in order to provide said biosensor zone or said biosensor zones with the electrical drive signal. The use of a single common supply unit reduces the production costs of the biosensor array.

In particular, for the configuration described last, the drive unit and/or the detection unit may be set up in such a way that an electrical reference signal can be applied to at least a portion of the nonselected biosensor zones by means of said drive unit and/or detection unit.

Consequently, by means of the supply unit, a voltage signal may be applied as an electrical drive signal to a single biosensor zone or, by way of example, a row of biosensor zones, and an electrical reference signal, in particular the electrical ground potential, may be applied to a portion or to all of the rest of nonselected biosensor zones.

As an alternative, the drive unit may have, for a respective group of biosensor zones, a supply unit that is associated with the respective group and is set up in such a way that it can be used to apply the electrical drive signal to the biosensor zones of the associated group.

By way of example, in the case of a matrix-type arrangement of the biosensor zones, for each column of sensor zones, a common voltage source may be provided as a supply unit associated with the biosensor zones arranged along the column. The drive unit and/or the selection unit may, in particular, be set up in such a way that in each case one of the supply units provides the associated group of biosensor zones with an electrical drive potential, whereas the other supply units provide the associated biosensor zones with a reference potential, for example the electrical ground potential.

The detection unit may have a measuring unit that is common to all the biosensor zones and is set up in such a way that it can be used to detect the electrical detection signal at precisely one selected biosensor zone.

In other words, it is possible, by way of example, to provide a common current detecting unit (e.g. ammeter) for all the biosensor zones, which is connected into a selected biosensor zone using the selection unit, so that in this case the electric current through the selected biosensor zone is detected by means of the measuring unit provided jointly for all the biosensor zones.

As an alternative, the detection unit may have, for a respective group of biosensor zones, a measuring unit that is associated with the respective group, each of the measuring units being set up in such a way that it can be used to detect the electrical detection signal at precisely one selected biosensor zone of the associated group.

With reference to the example of a matrix-type arrangement of biosensor zones, a common measuring unit (for example current detecting unit) may be provided for example for each row of biosensor zones. In this case, it is possible for example to read the selected biosensor zones of a column temporally in parallel by virtue of the measuring units for the selected biosensor zones arranged in different rows in each case separately detecting the electrical read-out signal.

Furthermore, the biosensor array according to the invention may have a potentiostat device set up in such a way that it can be used to predefine a constant electrical potential for at least a portion of the biosensor zones.

In particular, the potentiostat device may have a reference electrode, a counterelectrode and an operational amplifier, a first input of the operational amplifier being coupled to the reference electrode, a second input of the operational amplifier being coupled to a reference potential (for example the electrical ground potential) and an output of the operational amplifier being coupled to the counterelectrode.

The method according to the invention for operating the biosensor array according to the invention is described below. Refinements of the biosensor array also apply to the method for operating the biosensor array according to the invention.

Preferably, for the at least one selected biosensor zone on the basis of the drive signal and the detection signal, it is determined whether sensor events have taken place at the at least one selected biosensor zone and/or the quantity in which sensor events have taken place at the at least one selected biosensor zone.

The problem of the invention is solved in accordance with another aspect of the invention by means of a biosensor array and by means of a method for operating a biosensor array.

The biosensor array according to the invention in accordance with the other aspect of the invention has a substrate and a plurality of biosensor zones arranged on the substrate, each of which biosensor zones has a first terminal and a second terminal. Furthermore, the biosensor array contains at least one first signal line and at least one second signal line, the at least one first signal line being electrically insulated from the at least one second signal line. In each case the first terminal of each biosensor zone is coupled to precisely one of the at least one first signal line, and the second terminal of each biosensor zone is coupled to precisely one of the at least one second signal line. At least one of the at least one first signal and at least one of the at least one second signal line is coupled to at least two of the biosensor zones. Furthermore, provision is made of a first drive unit for providing a first electrical drive signal and a second drive unit for providing a second electrical drive signal. Moreover, the biosensor array contains a first detection unit coupled to the first drive unit and/or a second detection unit coupled to the second drive unit, which is or are set up in such a way that it detects or they detect a first and/or second electrical detection signal of a selected biosensor zone that results from the first and the second electrical drive signal. A selection unit is set up in such a way that it couples the first drive unit to the first signal line of a biosensor zone to be selected and the second drive unit to the second signal line of the biosensor zone to be selected, whereby the biosensor zone is selected.

Furthermore, the other aspect of the invention provides a method for operating a biosensor array having the features described above. In accordance with the method, the first drive unit is coupled to the first signal line of a biosensor zone to be selected and the second drive unit is coupled to the second signal line of the biosensor zone to be selected, whereby the at least one biosensor zone is selected. Furthermore, the first signal line of the selected biosensor zone is provided with a first electrical drive signal and the second signal line of the selected biosensor zone is provided with a second electrical drive signal. Moreover, a first detection signal resulting from the first or the second electrical drive signal is detected on the first signal line of the selected biosensor zone and/or a second detection signal resulting from the first and the second electrical drive signal is detected on the second signal line of the selected biosensor zone.

A basic idea of the invention consists in providing first signal lines and second signal lines that are provided jointly for in each case a plurality of biosensor zones of a biosensor array, thereby considerably reducing the number of signal lines required for operating the biosensor array. This makes it possible to operate a biosensor array (in particular on a passive chip) with a relatively small number of signal lines and a small number of pads coupled to the signal lines. This saves space on the biosensor array, which enables a higher integration density, and the production costs are reduced. The array architecture according to the invention can also be used in active chips since it permits the circuitry outlay per biosensor zone to be kept low, which in turn enables the production of high-density arrays. In the case of active biosensor arrays, additional circuit devices (for example preamplifiers, AD converters, etc.) are provided on the substrate.

For a, by way of example, matrix-type arrangement of the biosensor zones along second signal lines provided as row lines and along first signal lines provided as column lines, it is possible for e.g. m columns to be optionally coupled to an exciting first voltage source of the first drive unit or to electrical ground potential. The n rows may optionally be coupled to a second exciting voltage source of the second drive unit or to the electrical ground potential. The selection of the coupling of the terminals of the biosensor zones to the voltage sources or the ground potential is effected by means of the selection unit.

By way of example, a positive electrical voltage may be applied as a first electrical drive signal to precisely one column line and an electrical voltage having a negative sign may be applied as a second electrical drive signal to precisely one row line. Only a biosensor zone arranged in the crossover region between the selected row and the selected column has, between its two terminals (i.e. its two electrodes), a potential difference that is large enough to enable redox recycling processes to take place on the biosensor zone. All the other biosensor zones have, between their terminals, a potential difference corresponding to the first electrical voltage or to the second electrical voltage since the respective other terminal is at ground potential. As a result, at these biosensor zones, redox recycling processes are not possible or are not possible to a sufficient extent in order to generate a detectable temporally rising signal.

If, in the case of a selected biosensor zone, a sensor event, for example a hybridization event, occurs between capture molecules immobilized on the biosensor zone and particles of an analyte to be detected, redox recycling processes may occur using a label at the particles to be detected, a chemical component introduced into the analyte, and a sufficiently large electrical potential difference between the sensor electrodes. As a consequence thereof, an electric current in each case flows as a detection signal on the first signal line coupled to the selected biosensor zone and on the second signal line coupled to the selected biosensor zone. By detecting one value or preferably both values of the currents, the occurrence of hybridization events can be deduced.

For the case of a matrix-type arrangement of the biosensor zones with m columns and n rows, only n+m+2 terminals are required according to the invention, namely m first signal lines, n second signal lines and (optionally) two further terminals for reference electrode and counterelectrode of a potentiostat. Therefore, only 22 signal lines are required for a chip with, for example, 8×12=96 positions, and 82 signal lines are required for a chip with 32×48=1536 positions. This represents a considerable reduction of outlay compared with the prior art. The optimally achievable ratio of the number of terminals normalized to the number of sensor positions on the chip results for the case n=m, that is to say for a sensor array with a square architecture (number of rows=number of columns).

The invention clearly makes it possible to significantly reduce the production-technological outlay for a biosensor array by virtue of the fact that at least one of the at least one first signal line and at least one of the at least one second signal line is coupled to at least two of the biosensor zones. In other words, provision is made of signal lines for driving and detection that are common to a respective plurality of biosensor zones.

The biosensor array may have an evaluation unit set up in such a way that it determines for the at least one selected biosensor zone on the basis of the first and/or the second detection signal whether sensor events have taken place at the at least one selected biosensor zone and/or the quantity in which sensor events have taken place at the at least one selected biosensor zone.

At least one of the biosensor zones may be set up as an electrochemical biosensor zone. In particular, at least one of the biosensor zones may be a redox recycling biosensor zone.

In the case of a redox recycling biosensor zone, particles to be detected are preferably provided with a label which, after a hybridization event that has taken place with capture molecules immobilized on the sensor zone, is used for cleaving a substance that is to be introduced into the arrangement and is electrochemically inactive at the potentials used into two partial molecules, at least one of which is electrochemically active. This leads to an alteration of the electrical properties of the respective sensor position of the biosensor array.

The biosensor zone may have a first and a second electrode, the first electrode being coupled to the first terminal and the second electrode being coupled to the second terminal of the biosensor zone. The first and the second electrode are preferably an interdigital electrode. In other words, the first and/or the second electrode may be configured and operable like the first or second interdigital electrode 112, 113 shown in FIG. 1C.

The biosensor zones may be grouped to form a plurality of biosensor groups in such a way that each biosensor group can optionally be operated separately from the other biosensor groups or jointly with at least a portion of the other biosensor groups. Compartmentalization of the biosensor array is clearly possible. By way of example, if a partial region of the biosensor zones is sufficient for a specific application and the other biosensor zones are not required for this application, then the biosensor zones of the partial region may be grouped to form a group and this group may be operated separately from the rest of the biosensor zones.

The substrate may be a ceramic substrate, a semiconductor substrate (in particular a silicon substrate, i.e. a silicon wafer or a silicon chip), a glass substrate or a plastic substrate.

The first and the second electrical drive signal are preferably electrical DC voltage signals with different signs relative to a reference potential, which reference potential may be present at at least one terminal of a nonselected biosensor zone, and the first and/or the second electrical detection signal is preferably an electric current.

It is alternatively provided that the first and second electrical drive signals are voltage signals that are in antiphase with respect to one another. A condition for the occurrence of redox recycling processes at a selected sensor zone is merely that the potential difference between the first and the second electrical drive signal exceeds a certain threshold value.

Generally, an electrical reference potential (e.g. the ground potential) is applied to one terminal or to both terminals of a nonselected biosensor zone. However, it is also possible for at least one nonselected biosensor zone to be "floating", that is to say for the terminals of this biosensor zone not to be brought to a defined electrical potential.

The amplitudes and signs of the first and of the second electrical drive signal are preferably chosen in such a way that on account of a sensor event that has taken place at a biosensor zone, a significant first and/or second detection signal is generated essentially only when the first terminal of the biosensor zone is coupled to the first drive unit and simultaneously the second terminal of the biosensor zone is coupled to the second drive unit. In other words, the values of the first and second electrical drive signals are preferably chosen in such a way that a biosensor zone which is not to be selected, to whose first terminal the first drive signal is applied and to whose second terminal the second drive signal is not applied, is not capable of carrying out redox recycling processes. Furthermore, the values of the first and second electrical drive signals are preferably chosen in such a way that a biosensor zone which is not to be selected, to whose first terminal the first drive signal is not applied and to whose second terminal the second drive signal is applied, is not capable of carrying out redox recycling processes. Only those biosensor zones at whose first terminal the first drive signal is present and at whose second terminal the second drive signal is present are selected.

It is advantageous to configure the biosensor array according to the invention as an active sensor chip that may contain integrated circuits having any desired functions. An analog-to-digital converter circuit may be integrated in the substrate of the biosensor array, which circuit is set up in such a way that it converts an analog electrical signal into a digital signal and provides it to the evaluation unit. Furthermore, an electrical supply unit may be integrated in the substrate, which supply unit is set up in such a way that it can provide electrical voltage signals and/or electric current signals to the first and/or the second drive unit and/or to the selection unit. Moreover, a digital-to-analog converter circuit may be integrated in the substrate, which circuit is set up in such a way that it can convert a digital signal of the supply unit into an analog signal and provide it to the drive unit and/or to the selection unit. It is also possible to provide an input/output interface for the connection of an external apparatus on the biosensor array. This may be set up for example as a digital I/O interface. Furthermore, an amplifier unit, set up for amplifying the first and/or the second electrical detection signal, may be integrated in the substrate. Amplification "on-chip" avoids the situation wherein an analog signal that is susceptible to interference runs along a long signal line and is therefore exposed to interference. As a result, the signal-to-noise ratio is improved.

Preferably, the at least one first signal line, on the one hand, and the at least one second signal line, on the other hand, are at least partly formed in two different conductor planes (e.g. metallization planes) in and/or on and/or below the substrate. The use of two different line planes enables an electrically insulated line crossover between first and second signal lines. The two line planes (in particular metal planes) may be realized in the manner known from processes appertaining to microelectronics. In that case, the metal planes are often embedded in intermetal dielectrics above the bulk material (the substrate). As an alternative, however, it is also possible for one of the line planes to be realized in the same plane (and preferably from the same material) as the transducer elements themselves (e.g. gold material of interdigital electrodes). In other words, the biosensor zones may be formed in precisely one of the line planes.

Furthermore, in a first line section, in which the at least one first signal line and the at least one second signal line are free of a mutual crossover, the at least one first signal line and the at least one second signal line may be formed such that they run in the same plane. Furthermore, in a second line section, in which the at least one first signal line and the at least one second signal line mutually cross one another, the at least one first signal line and the at least one second signal line may be formed such that they run in different planes.

In other words, a second conductor plane need not necessarily be provided in a buried fashion with regard to a first conductor plane. It is also possible to realize both planes partly in the same plane as the transducers (and to produce them from the same material as the transducers). It is only in crossover regions between first and second signal lines that a bridging of the crossover region is then necessary in order to ensure an electrical insulation between drive lines and detection lines. Between the line sections running in the bridging region in different planes, it is preferable to use an electrically insulating material between the lines.

Preferably, the first line section of the at least one first signal line and/or of the at least one second signal line is coupled to the second line section of the at least one first signal line and/or of the at least one second signal line by means of at least one electrical contact-connection element arranged in a manner essentially running vertically with respect to the substrate. In particular, vias are possible in order to couple line sections of a first signal line (and/or of a second signal line) that run in different planes in each case to one another.

The at least one first signal line and/or the at least one second signal line may be formed in a manner running on an underside of the substrate or beneath the substrate.

In other words, a line plane may be realized for example also on the underside of a substrate (e.g. printed circuit board). Plated-through holes are necessary for this purpose. Furthermore, a dielectric layer may be formed beneath the substrate, electrically conductive structures being embedded in said dielectric layer in order to form signal lines.

The biosensor zones of the biosensor array according to the invention may essentially be arranged in a rectangular, preferably square, hexagonal or triangular matrix. A matrix-type rectangular arrangement of the biosensor zones with an identical number of rows and columns (square matrix) enables a particularly favorable ratio of the number of required signal lines (and pads) to the number of biosensor zones.

The drive unit may have a first supply unit that is common to all the biosensor zones and/or the second drive unit may have a second supply unit that is common to all the biosensor zones, the first supply unit being set up in such a way that it can be used to apply the first electrical drive signal to the at least one selected biosensor zone, and/or the second supply unit being set up in such a way that it can be used to apply the second electrical drive signal to the at least one selected biosensor zone.

In other words, it is possible, by way of example, to provide a single common voltage source as a first supply unit or a single common voltage source as a second supply unit, which, using the functionality of the selection unit, is coupled to in each case a biosensor zone or a portion of the biosensor zones (for example a column or row of biosensor zones) in order to provide said biosensor zone or said biosensor zones with the corresponding electrical drive signal. The use of a single common first supply unit or a single common second supply unit reduces the production costs of the biosensor array.

The first and second drive units may be set up in such a way that an electrical reference signal can be applied to at least a portion of the nonselected biosensor zones, the value of said electrical reference signal essentially being the average value of the first and the second drive signal. Redox recycling processes can take place at a selected biosensor zone only when the first drive signal is applied to the first terminal thereof and the second drive signal preferably having an opposite sign is applied to the second terminal thereof, since the occurrence of redox recycling processes requires a sufficiently large potential difference between the terminals. By using the arithmetic mean of the first and the second electrical drive signal (or a voltage near to the arithmetic mean) as a reference potential for the biosensor zones which are not to be selected, it is ensured that undesirable redox recycling processes are avoided at nonselected biosensor zones. In other words, an electrical reference potential (e.g. the ground potential) is often applied to one terminal or to both terminals of a nonselected biosensor zone. However, it is also possible for at least one nonselected biosensor zone to be "floating", i.e. for the terminals of this biosensor zone not to be brought to a defined electrical potential.

The first drive unit may have, for a respective first group of biosensor zones, a first supply unit that is associated with the respective group, which first supply unit is set up in such a way that it can be used to apply the first electrical drive signal to the biosensor zones of the associated first group, and/or the second drive unit may have, for a respective second group of biosensor zones, a second supply unit that is associated with the respective group, which second supply unit is set up in such a way that it can be used to apply the second electrical drive signal to the biosensor zones of the associated second group.

By way of example, in the case of a matrix-type arrangement of the biosensor zones, for each column of sensor zones, a common voltage source may be provided as a supply unit associated with the biosensor zones arranged along a column. Furthermore, for each row of sensor zones, another common voltage source may be provided as a second supply unit associated with the biosensor zones arranged along the row.

The drive units or the selection unit may, in particular, be set up in such a way that in each case one of the supply units provides the associated group of biosensor zones with an electrical drive signal, whereas the other supply units provide the associated biosensor zones with a reference potential, for example the electrical ground potential.

The first detection unit may have a first measuring unit (for example an ammeter) that is common to all the biosensor zones, which first measuring unit is set up in such a way that it is can be used to detect the electrical first detection signal at precisely one selected biosensor zone. As an alternative or supplementarily, the second detection unit may have a second measuring unit (for example an ammeter) that is common to all the biosensor zones, which second measuring unit is set up in such a way that it can be used to detect the electrical second detection signal at precisely one selected biosensor zone.

The first detection unit may have, for a respective third group of biosensor zones, a first measuring unit that is associated with the respective third group, each of the first measuring units being set up in such a way that it can be used to detect the electrical first detection signal at precisely one selected biosensor zone of the associated third group.

Furthermore, the second detection unit has, for a respective fourth group of biosensor zones, a second measuring unit that is associated with the respective fourth group, each of the second measuring units being set up in such a way that it can be used to detect the electrical second detection signal at precisely one selected biosensor zone of the associated fourth group.

Furthermore, the biosensor array according to the invention may have a potentiostat device set up in such a way that it can be used to predefine a constant electrical potential for at least a portion of the biosensor zones.

In particular, the potentiostat device may have a reference electrode, a counterelectrode and an operational amplifier, a first input of the operational amplifier being coupled to the reference electrode, a second input of the operational amplifier being coupled to a reference potential (for example the electrical ground potential) and an output of the operational amplifier being coupled to the counterelectrode.

Furthermore, a respective dedicated first DC voltage source may be provided for each row of biosensor zones and a respective dedicated second DC voltage source may be provided for each column of biosensor zones. Moreover, a respective dedicated first current detecting unit may be provided for each row of biosensor zones and a respective dedicated second current detecting unit may be provided for each column of biosensor zones. The sensor events can then be jointly detected simultaneously for all the biosensor zones by detecting summation currents in all the rows and columns.

Using a suitable correlation calculation, the individual sensor signals of the individual biosensor zones can be deduced from correlated row and column currents. This functions particularly well if, in a specific operating state, only very few or even just a single biosensor zone has a sensor signal. In the latter case, an electric current can be detected essentially only in a row line and a column line, so that it is possible to deduce a sensor event in the biosensor zone in the crossover region between the row line and the column line.

The method according to the invention for operating the biosensor array according to the invention is described below. Refinements of the biosensor array also apply to the method for operating the biosensor array according to the invention.

Preferably, for the at least one selected biosensor zone on the basis of the first and/or the second detection signal, it is determined whether sensor events have taken place at the at least one selected biosensor zone and/or the quantity in which sensor events have taken place at the at least one selected biosensor zone.

By way of example, if the biosensor zones are configured as redox recycling biosensor zones, and if a first DC voltage is chosen as the first drive signal and a second DC voltage having an inverse sign with respect to the first DC voltage is chosen as the second drive signal, then a hybridization event that has taken place at a selected redox recycling biosensor zone may be detected by virtue of the fact that redox recycling processes are generated at the selected redox recycling biosensor zone on account of the sufficiently strong voltage applied between the electrodes of said biosensor zone. This is detected by detecting an electric current on one of the signal lines or on both signal lines, the value and the time dependence of the current yielding information about whether a sensor event has taken place at the selected biosensor zone and/or the quantity in which sensor events have taken place there. As a result, it is possible to determine whether an analyte to be examined contains particles to be detected, and, if appropriate, the concentration in which the particles to be detected are contained in the analyte.

In different exemplary embodiments, identical components are provided with identical reference symbols.

A description is given below, referring to FIG. 6, of a biosensor array 600 in accordance with a first exemplary embodiment of the invention.

The biosensor array 600 has a silicon substrate 601 and four impedance biosensor zones 602 arranged in matrix form on the silicon substrate 601. Each of the impedance biosensor zones 602 has a first terminal 603 and a second terminal 604. Furthermore, the biosensor array 600 contains two drive lines 605 and two detection lines 606, the drive lines 605 being electrically insulated from the detection lines 606 (in particular in crossover regions 610). In each case the first terminal 603 of each impedance biosensor zone 602 is coupled to in each case precisely one of the two drive lines 605. In each case the second terminal 604 of each impedance biosensor zone 602 is coupled to precisely one of the two detection lines 606. In other words, in each case one of the two drive lines 605 is jointly provided for the impedance biosensor zones 602 arranged in the associated column. As a result, a total of four signal lines 605, 606 are required in order to electrically contact-connect the four impedance biosensor zones 602. Furthermore, the biosensor array contains a drive unit 607 for providing an electrical drive signal and a detection unit 608 for detecting an electrical detection signal resulting from the electrical drive signal. A selection unit 609 is set up in such a way that it couples the drive unit 607 to the drive line 605 of an impedance biosensor zone 602a that is to be selected and the detection unit 608 to the detection line 606 of the impedance biosensor zone 602a that is to be selected, whereby the impedance biosensor zone 602a is selected. By means of the selection unit 609, which is symbolized schematically in FIG. 6 by a first switching device 609a and a second switching device 609b, in accordance with the exemplary embodiment described, in each case precisely one of the impedance biosensor zones 602 is selected by virtue of the selection unit 609 coupling the selected biosensor zone, the biosensor zone 602a in accordance with the scenario shown in FIG. 6, to the drive unit 607 and to the detection unit 608 in such a way that an electrical drive signal is applied to the selected impedance biosensor zone 602a by means of the drive unit 607, and that an electrical detection signal resulting from the electrical drive signal can be detected at the selected impedance biosensor zone 602a by means of the detection unit 608. In the case of the biosensor array 600, by changing over the switch of the first switching device 609a, the drive unit 607 can be coupled to the left-hand drive line 605 in accordance with FIG. 6 and/or to the right-hand drive line 605 in accordance with FIG. 6. Furthermore, by means of the second switching device 609b, the detection unit 608 can be coupled to the upper detection line in accordance with FIG. 6 and/or to the lower detection line in accordance with FIG. 6. Furthermore, by means of the switching devices 609a, 609b, at least one drive line 605 can be brought to electrical ground potential 611, and/or at least one detection line 606 can be brought to electrical ground potential 611. In accordance with the switch positions of the switches of the switching devices 609a, 609b in the operating state shown in FIG. 6, the right-hand drive line 605 and the upper detection line 606 are at ground potential 611.

It should be noted that the switch position of the first and second switching devices 609a, 609b can be switched over or controlled on the basis of the functionality of the selection unit 609.

Figure 6:
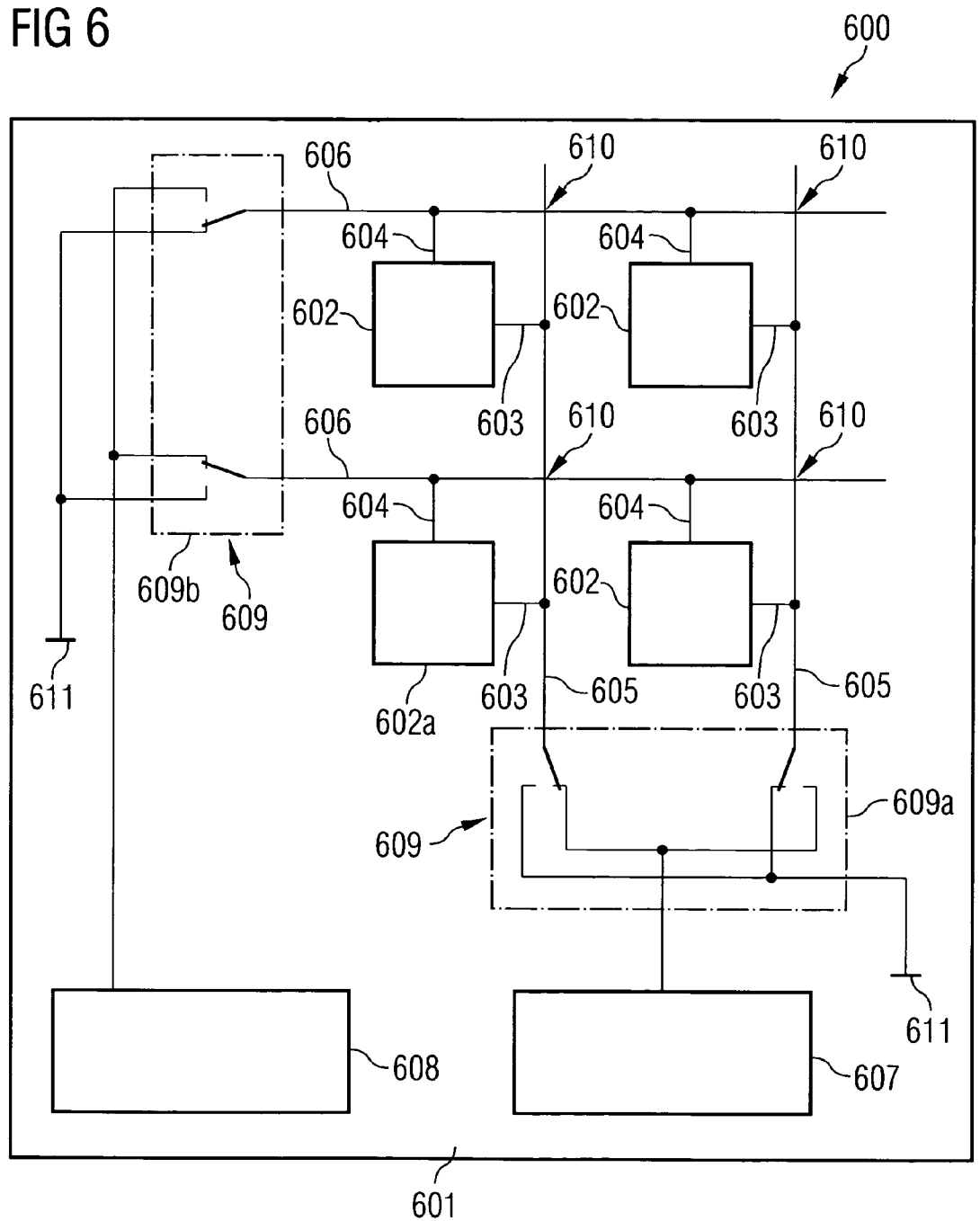
FIG. 6 shows a biosensor array in accordance with a first exemplary embodiment of the invention.

In accordance with the scenario shown in FIG. 6, the switch position of the first switching device 609a is chosen in such a way that the drive unit 607 provides the electrical drive signal to the two left-hand impedance biosensor zones 602, 602a in accordance with FIG. 6. Furthermore, in accordance with the scenario shown in FIG. 6, the switch position of the second switch device 609b is chosen in such a way that the detection unit 608 is coupled to the two lower impedance biosensor zones 602a, 602 in accordance with FIG. 6. Only the selected impedance biosensor zone 602a is coupled both to the drive unit 607 and to the detection unit 608 and is therefore selected. Consequently, the selected impedance biosensor zone 602a is provided with the electrical drive signal by means of the drive unit 607, and an electrical detection signal of the selected impedance biosensor zone 602a that results from the electrical drive signal is detected by means of the detection unit 608.

In accordance with the exemplary embodiment of the invention as shown in FIG. 6, the biosensor zones are realized as impedance biosensor zones. In particular, each of the impedance biosensor zones 602 is configured like the interdigital electrode arrangement 100 described with reference to FIG. 1A to FIG. 5B. The first terminal 603 is coupled to the first electrode structure 102, and the second terminal 604 is coupled to the second electrode structure 103. The electrical drive signal is an AC voltage that is generated and provided by the drive unit 607. On the basis of said AC voltage, an AC current is generated in the selected impedance biosensor zone 602a, which is detected by means of an ammeter of the detection unit 608. The value of the impedance can be determined from the values of the AC voltage and the AC current.

Said value changes significantly, as described above, on account of a hybridization event at an impedance biosensor zone 602, so that, by detecting the value of the impedance before and after a hybridization event (that is to say before and after an analyte that possibly has particles to be detected has been filled into the biosensor array 600), the occurrence of hybridization events can be determined qualitatively or quantitatively.

A description is given below, referring to FIG. 7, of a biosensor array 700 in accordance with a second exemplary embodiment of the invention.

In the case of the biosensor array 700, a multiplicity of impedance biosensor zones 602 are arranged in matrix form on a silicon substrate 601. The biosensor array 700 has n rows and m columns of impedance biosensor zones 602 arranged in matrix form, that is to say m×n impedance biosensor zones. Furthermore, as shown in FIG. 7, m drive lines 605 and n detection lines 606 are provided, that is to say n+m signal lines. An impedance biosensor zone 602 configured as an interdigital electrode arrangement is in each case arranged in the crossover region between a respective drive line 605 and a respective detection line 606. The drive circuit 607 has an AC voltage source 701 and a further terminal, at which an electrical ground potential 702 is provided. The first switching device 609a has m first switches 703, each of which is coupled to one of the drive lines 605. A column of impedance biosensor zones 602 is selected by virtue of the impedance biosensor zones 602 of the column being coupled to the AC voltage source 601. On account of correspondingly chosen switch positions of the first switches 703, all the other columns of impedance sensor zones 602 are coupled to the electrical ground potential 702, as shown in FIG. 7. In accordance with the scenario shown in FIG. 7, only the impedance biosensor zones 602 in the second column from the left are coupled to the AC voltage source 701.

The detection unit 608 has a current detecting unit 704, and is furthermore set up in such a way that it can provide an electrical ground potential 702. As is furthermore shown in FIG. 7, the detection unit 608 is coupled to the detection lines 606 by means of the second switching device 609b. Second switches 705 are in each case situated in a switch position such that, by means of the second switching device 609b, precisely one of the detection lines 606 is coupled to the current detecting device 704, whereas all the other detection lines 606 are at electrical ground potential 702. In accordance with the scenario shown in FIG. 7, only the impedance biosensor zones 602 in the second row from the top are coupled to the current detecting device 704.

Figure 7:
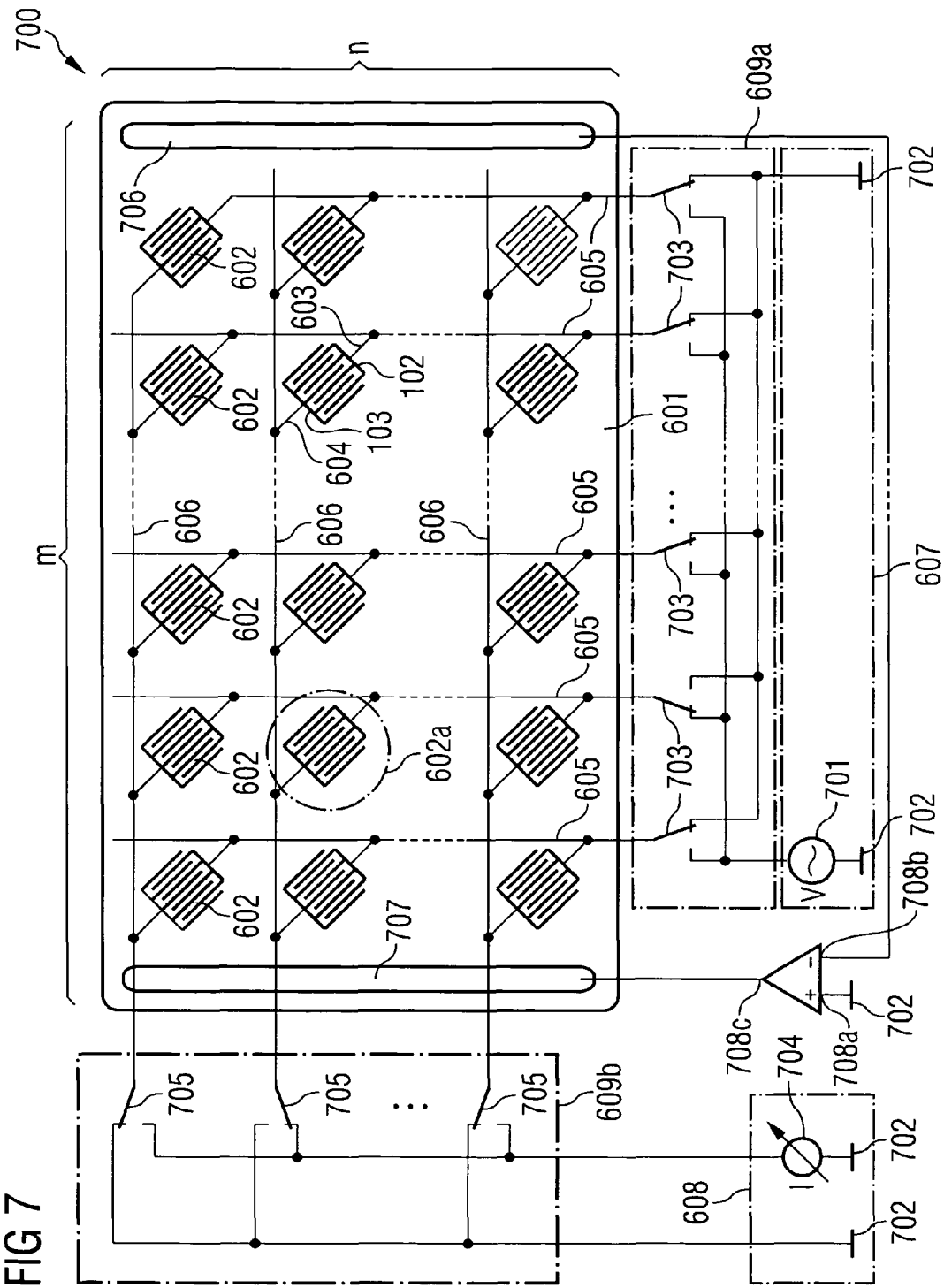
FIG. 7 shows a biosensor array in accordance with a second exemplary embodiment of the invention.

Consequently, in accordance with the scenario shown in FIG. 7, only the impedance biosensor zone 602a arranged in the second row and the second column is selected. In accordance with the scenario shown in FIG. 7, an electrical AC voltage is applied to the impedance biosensor zone 602a by means of the AC voltage source 701. This results in an electric AC current, which is detected by the current detecting device 704. If the impedance of the impedance biosensor zone 602a changes on account of a hybridization event, then this leads to an alteration of the value of the AC current, which is detected by the current detecting device 704. It is thereby possible to determine whether or not a sensor event has taken place at the selected impedance biosensor zone 602a.

Furthermore, the biosensor array 700 has a potentiostat device. The latter is constructed from a reference electrode 706 on the substrate 601, a counterelectrode 707 on the substrate 701, and an operational amplifier 708 arranged outside the chip ("off-chip"). A noninverting input 708a of the operational amplifier 708 is at electrical ground potential 702. An inverting input 708b is electrically coupled to the reference electrode 706, and an output 708c of the operational amplifier 708 is coupled to the counterelectrode 707. These components together form a potentiostat circuit. Although in the case of impedance sensors, when operated properly, it is possible to prevent undesirable electrochemical conversions from occurring at the electrode structures, the configuration shown in FIG. 7 can advantageously be utilized for allocating to an analyte introduced into the biosensor array 700 a stable electrochemical potential in a low-resistance manner (cf. WO 93/22678, DE 19610115 A1, U.S. Patent Ser. No. 60/007840, and Peter Van Gerwen et al.). The configuration with a potentiostat device is particularly advantageous when the biosensor zones are embodied as redox recycling sensors.

A description is given below, referring to FIG. 8, of an equivalent circuit diagram 800 of the biosensor array shown in FIG. 7.

Figure 8:
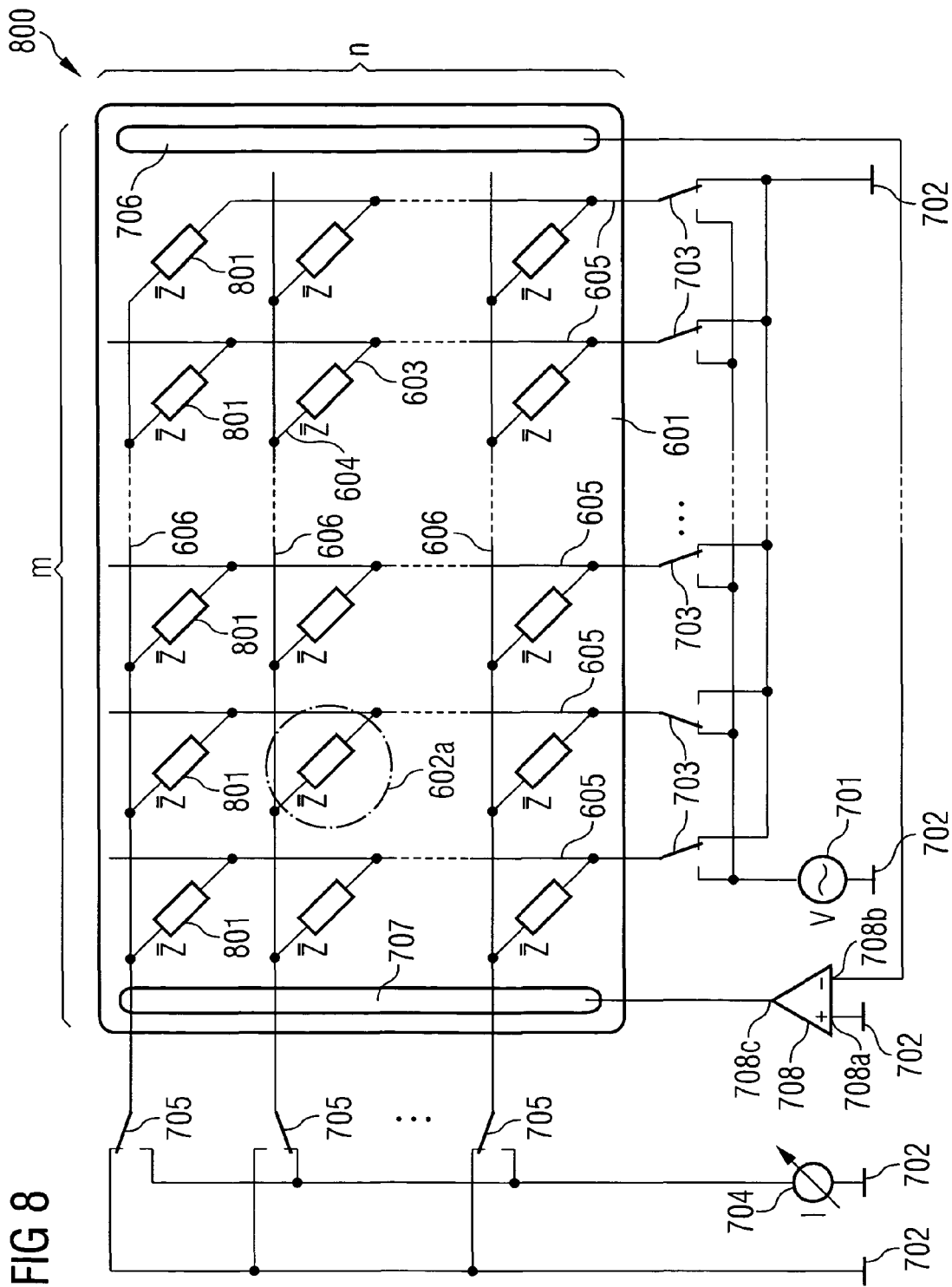
FIG. 8 shows an equivalent circuit diagram of the biosensor array shown in FIG. 7.

In FIG. 8, the impedance biosensor zones 602 configured as an interdigital electrode arrangement are replaced in circuitry terms by an impedance $\overline{Z}$ 801 (a complex quantity) since the impedance biosensor zones 602 configured as an interdigital electrode arrangement contain a resistive and capacitive component of the impedance.

Figure 5B:
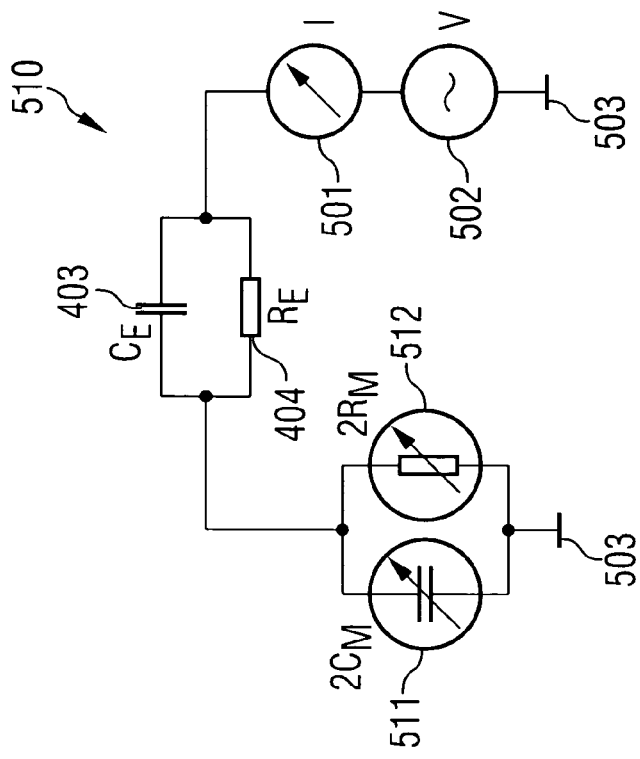
FIGS. 5A, 5B show equivalent circuit diagrams of the first partial region of the interdigital electrode arrangement in accordance with the prior art as shown in FIG. 1.
Figure 5A:
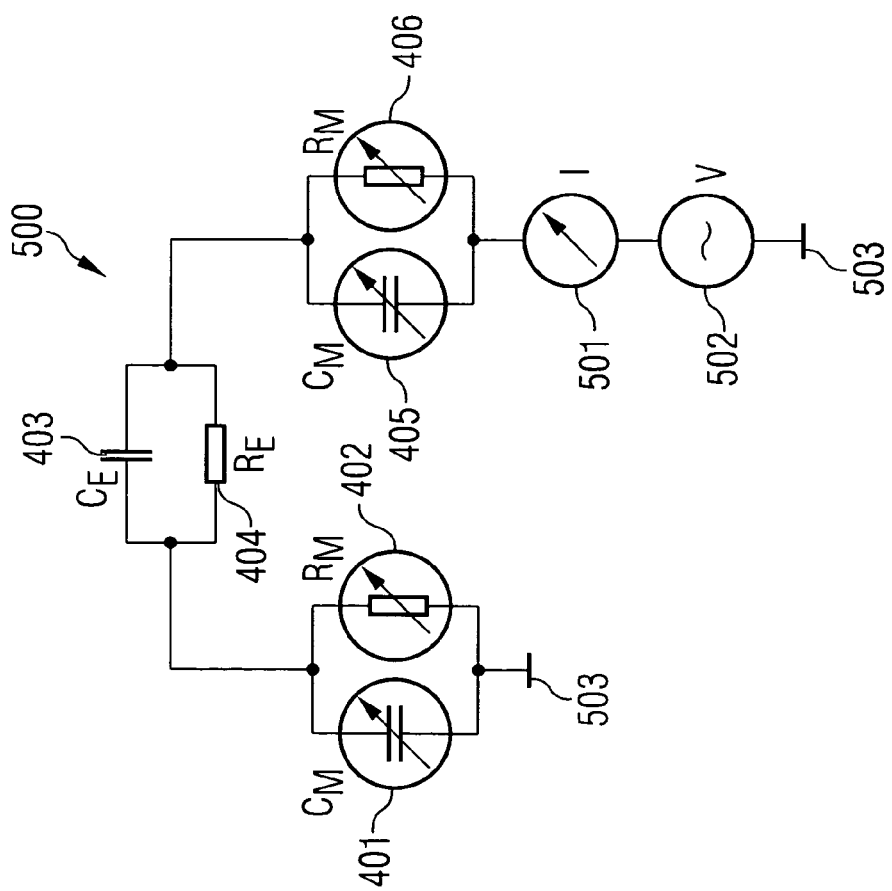
Figure 9:
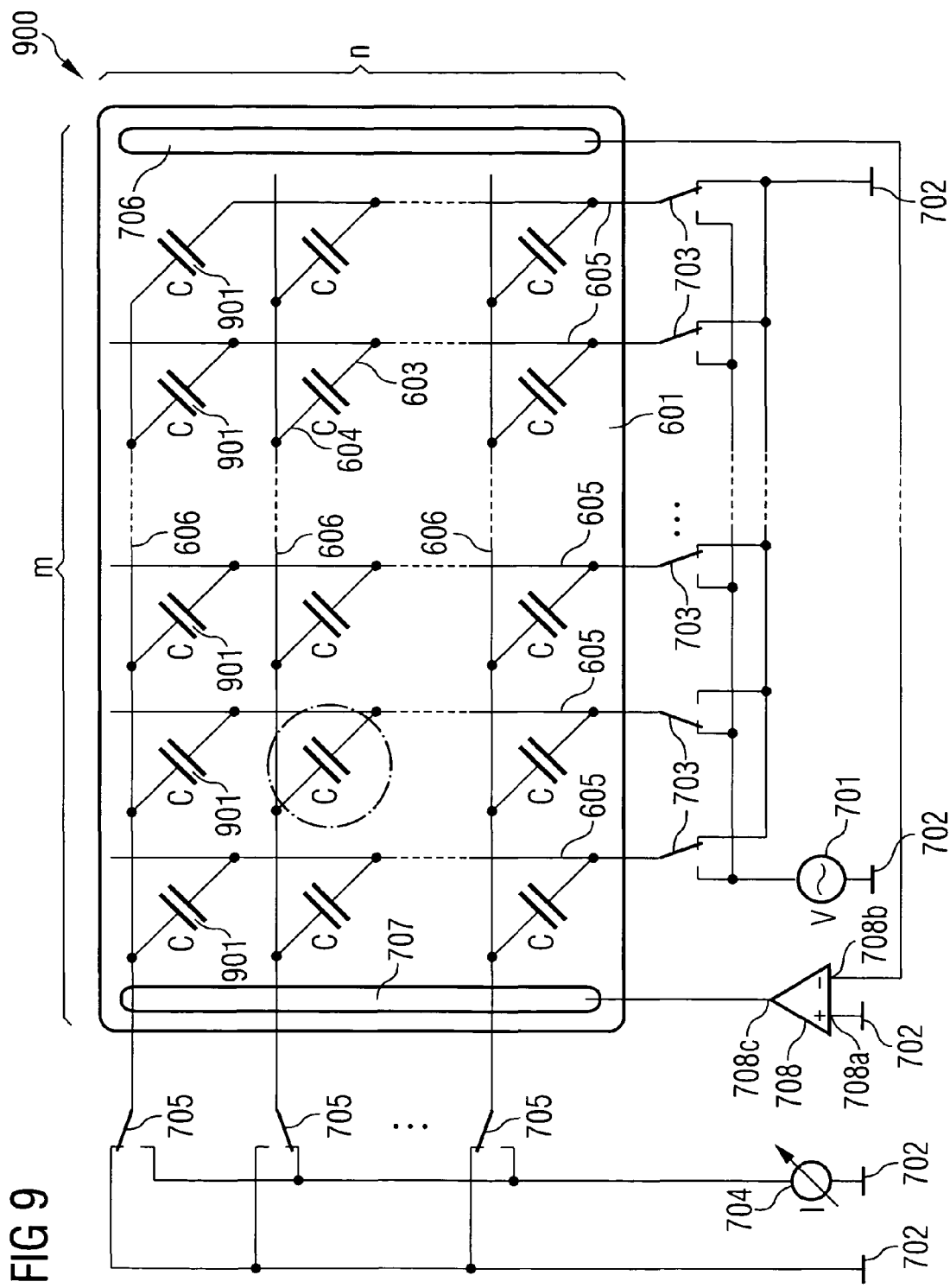
FIG. 9 shows a simplified equivalent circuit diagram of the biosensor array shown in FIG. 7.

FIG. 9 shows a simplified equivalent circuit diagram 900 of the biosensor array 700, which uses the approximation—which is often valid to a good approximation—that in the impedance $\overline{Z}$ of impedance biosensor zones, the capacitive component is dominant over the resistive component, so that the resistive component is approximately negligible. Therefore, the impedance 801 from FIG. 8 is approximated by a capacitance C 901 in FIG. 9. In the illustration of FIG. 5A, FIG. 5B, this corresponds to the assumption that the parallel-connected components $C_M$, $R_M$ have values such that $R_M$ is negligible with respect to $C_M$.

A description is given below, referring to FIG. 10, of a biosensor array 1000 in accordance with a third exemplary embodiment of the invention.

In the case of the biosensor array 1000, in a departure from the biosensor array 700, a separate AC voltage source 701 (V1, V2, . . . , Vm-1, Vm) is provided for each column of impedance biosensor zones 602. Furthermore, in a departure from the biosensor array 700, in the case of the biosensor array 1000, a separate current detecting device 704 (I1, I2, . . . , In-1, In) is provided for each row of impedance biosensor zones 602. Each of the AC voltage sources 701 may provide the associated column of impedance biosensor zones 602 with an AC voltage, in a specific operating state in each case only one of the AC voltage sources V1, V2 . . . Vm-1, Vm providing an AC voltage, whereas the other voltage sources thereof are inactive. In other words, apart from one of the AC voltage sources 701, all the others are switched off, so that all but one of the drive lines 605 are at ground potential 702. This selection of a respectively activated voltage source 701 is effected by means of the selection unit, which is clearly embodied in one piece with the drive unit in accordance with the exemplary embodiment shown in FIG. 10. In other words, the functionality described is performed by the drive/selection unit 1001.

Figure 10:
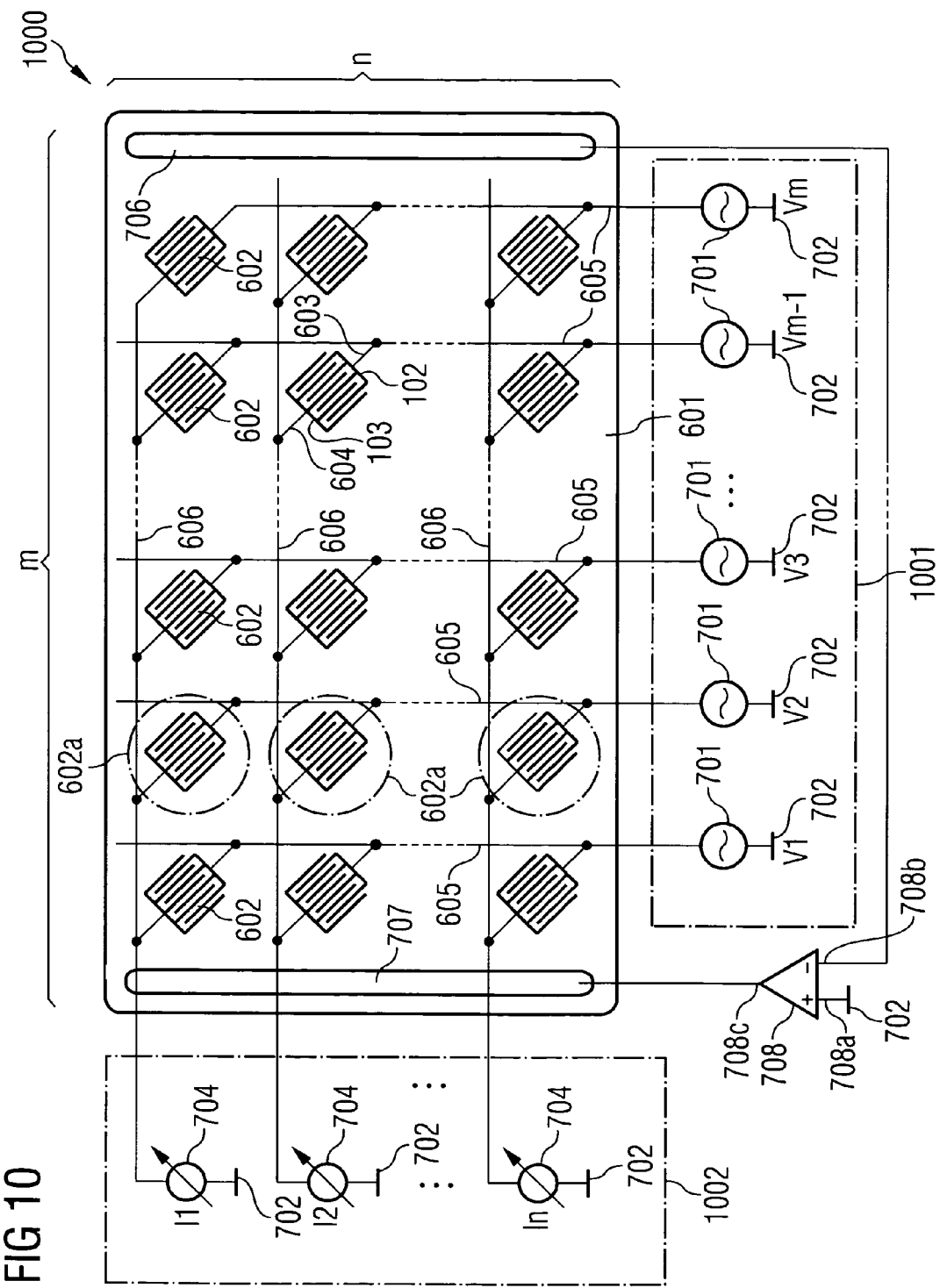
FIG. 10 shows a biosensor array in accordance with a third exemplary embodiment of the invention.

In accordance with the scenario shown in FIG. 10, all the impedance biosensor zones 602a arranged in the second column are selected since only the AC voltage source V2 provides an AC voltage. By contrast, the AC voltage sources V1, V3, V4, . . . Vm-1, Vm are deactivated, so that the associated drive lines 605 are at electrical ground potential 702. During operation of the biosensor array 1000, all but precisely one voltage source (V2 in accordance with the present scenario in FIG. 10) supply electrical ground potential 701, whereas the voltage source V2 702 functions as a stimulus for the corresponding column of impedance biosensor zones 602a.

Since each row is provided with a separate current detecting device 704, the rows can be read temporally in parallel in the case of the biosensor array 1000. By way of example, the selected impedance biosensor zone 602a of the first row may be read by means of the current detecting device I1, the selected impedance biosensor zone 602a of the second row may be read temporally in parallel by means of the current detecting device I2, etc.

As an alternative, a sequential read operation is also possible. In this case, the detection/selection unit 1002 is set up in such a way that it selects which of the current detecting devices I1, I2, ... In detects an AC current resulting from the AC voltage (for example from the voltage source V2).

Figure 11:
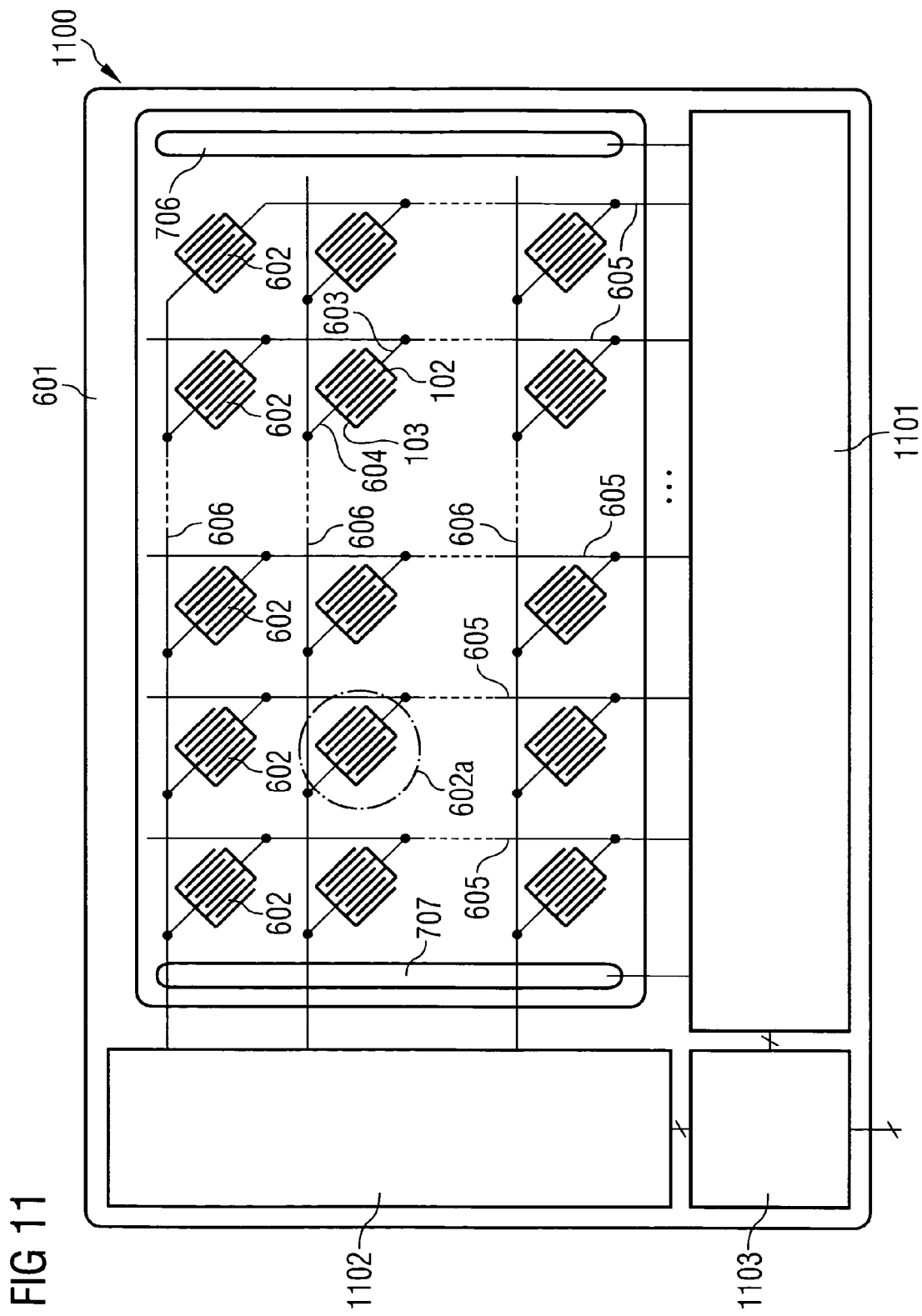
FIG. 11 shows a biosensor array in accordance with a fourth exemplary embodiment of the invention.

A description is given below, referring to FIG. 11, of a biosensor array 1100 in accordance with a fourth exemplary embodiment of the invention.

The biosensor array 1100 has a first circuit block 1101 and a second circuit block 1102 and also an input/output interface 1103 coupled to the two circuit blocks 1102, 1103. A sensor signal, for example the electrical drive signal and the electrical detection signal, may be provided at the input/output interface.

The biosensor array 1100 represents a so-called active chip. This is understood to mean a semiconductor substrate into which circuits that may have different functions are integrated monolithically. In particular the components voltage sources 701, operational amplifiers 708 and parts of the selection unit 709 are integrated in the first circuit block 1101, and other components such as the current detecting device 704, other parts of the selection unit 609, etc. are integrated in the second circuit block 1102. Furthermore, further components for the signal preprocessing and signal further processing are realized "on-chip" in the circuit blocks 1101, 1102. Furthermore, the chip of the biosensor array 1100 has a defined (e.g. digital) interface 1103 (I/O) configured in accordance with the requirements of the respective application.

The use of the architecture according to the invention on active chips may be advantageous for example if a large number of relatively small-area interdigital structures are used whose area no longer permits an active circuit for controlling the respective sensor to be realized beneath each sensor. Furthermore, particular advantages are afforded if the requirements made of the performance of the circuits that are realized on-chip are very high. This last is applicable particularly when the area of a sensor element has a crucial influence on the performance (for example the noise).

Figure 12:
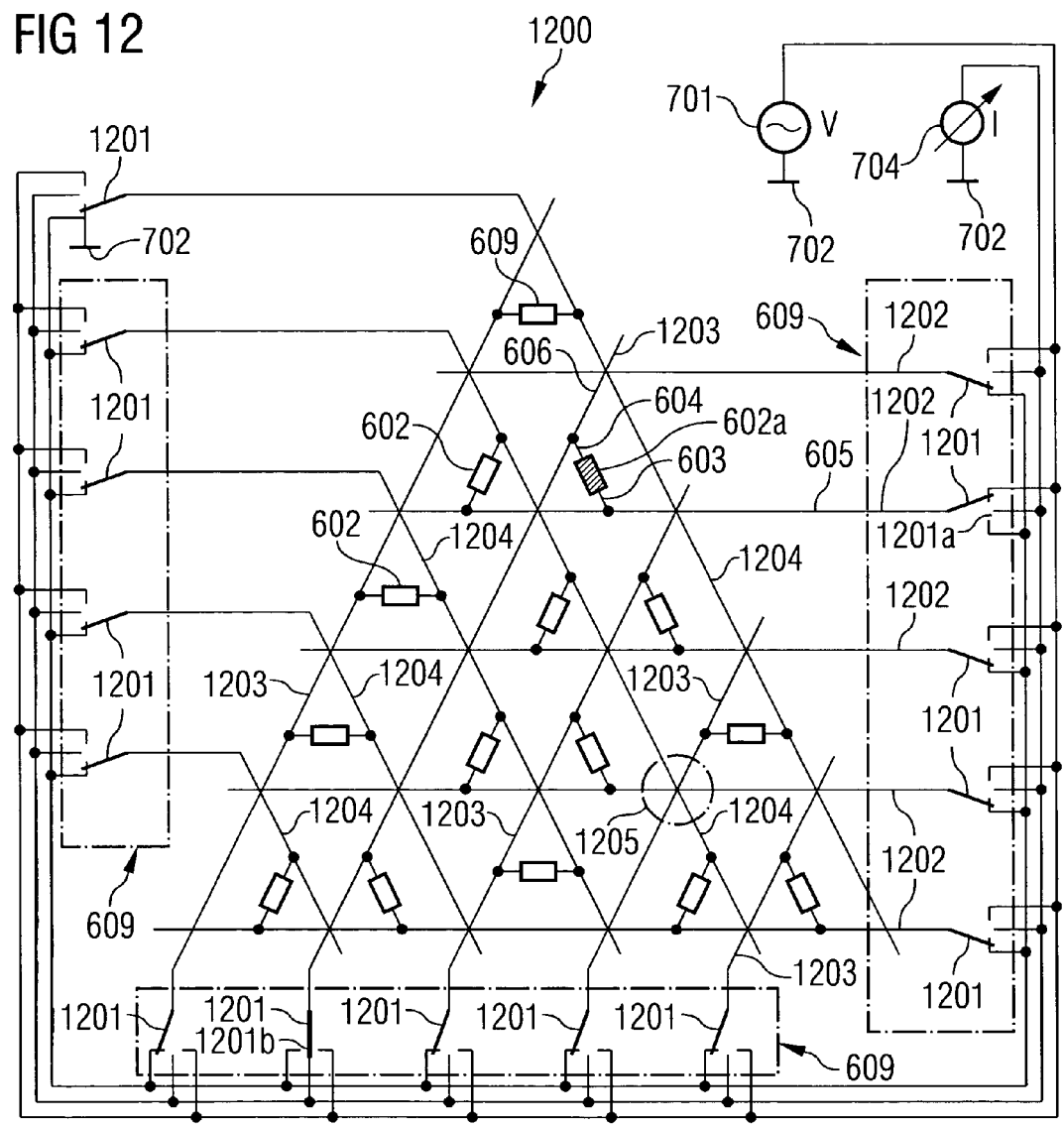
FIG. 12 shows a biosensor array in accordance with a fifth exemplary embodiment of the invention.

A description is given below, referring to FIG. 12, of a biosensor array 1200 in accordance with a fifth exemplary embodiment of the invention.

The biosensor array 1200 is an arrangement of impedance biosensor zones 602 which is provided as a triangular matrix with three wiring directions. Furthermore, a common AC voltage source 701 is provided as a drive unit and a common current detecting device 704 is provided as a detection unit. The selection unit 609 is symbolized by means of a multiplicity of switches 1201 with controllable switch positions. The switch positions are controllable by means of the selection unit 609. Furthermore, in FIG. 12, first signal lines 1202, second signal lines 1203 and third signal lines 1204 are arranged such that they run in such a way that, in crossover regions (which are electrically insulated from one another) of the signal lines 1202 to 1204, the latter cross one another at angles of 60°. In particular, FIG. 12 shows a selected impedance biosensor zone 602a, which is selected on account of the switch positions of the switches 1201 as shown in FIG. 12. A first switch 1201a is in a switch position such that the first terminal 603 of the selected impedance biosensor zone 602a is coupled to the AC voltage source 701. Furthermore, a second switch 1201b is in a switch position such that the second terminal 604 of the selected impedance biosensor zone 602a is coupled to the current detecting device 704. The switch positions of all the other switches 1200 are such that the first, second and third signal lines 1202 to 1204 adjoining these other switches 1200 are at electrical ground potential 702. In other words, in accordance with the scenario shown in FIG. 12, the selected impedance biosensor zone 602a is the only one of the impedance biosensor zones 602 which is coupled both to the AC voltage source 701 and to the current detecting device 704. In accordance with the scenario shown in FIG. 12, the first signal line 1202 connected to the selected impedance biosensor zone 602a functions as a drive line 605, and the second signal line 1203 connected to the selected impedance biosensor zone 602a functions as a detection line 606. Each of the switches 1201 has three switch positions, so that the respectively associated signal line 1202 to 1204 can optionally be coupled to the electrical ground potential 702, the AC voltage source 701 or the current detecting device 704. As a result, an independent measurement is possible on each position of the impedance biosensor zones 602.

A description is given below, referring to FIG. 13, of how a crossover region 1205 between one of the first signal lines 1202, one of the second signal lines 1203 and one of the third signal lines 1204 can be realized using just two wiring planes.

Figure 13:
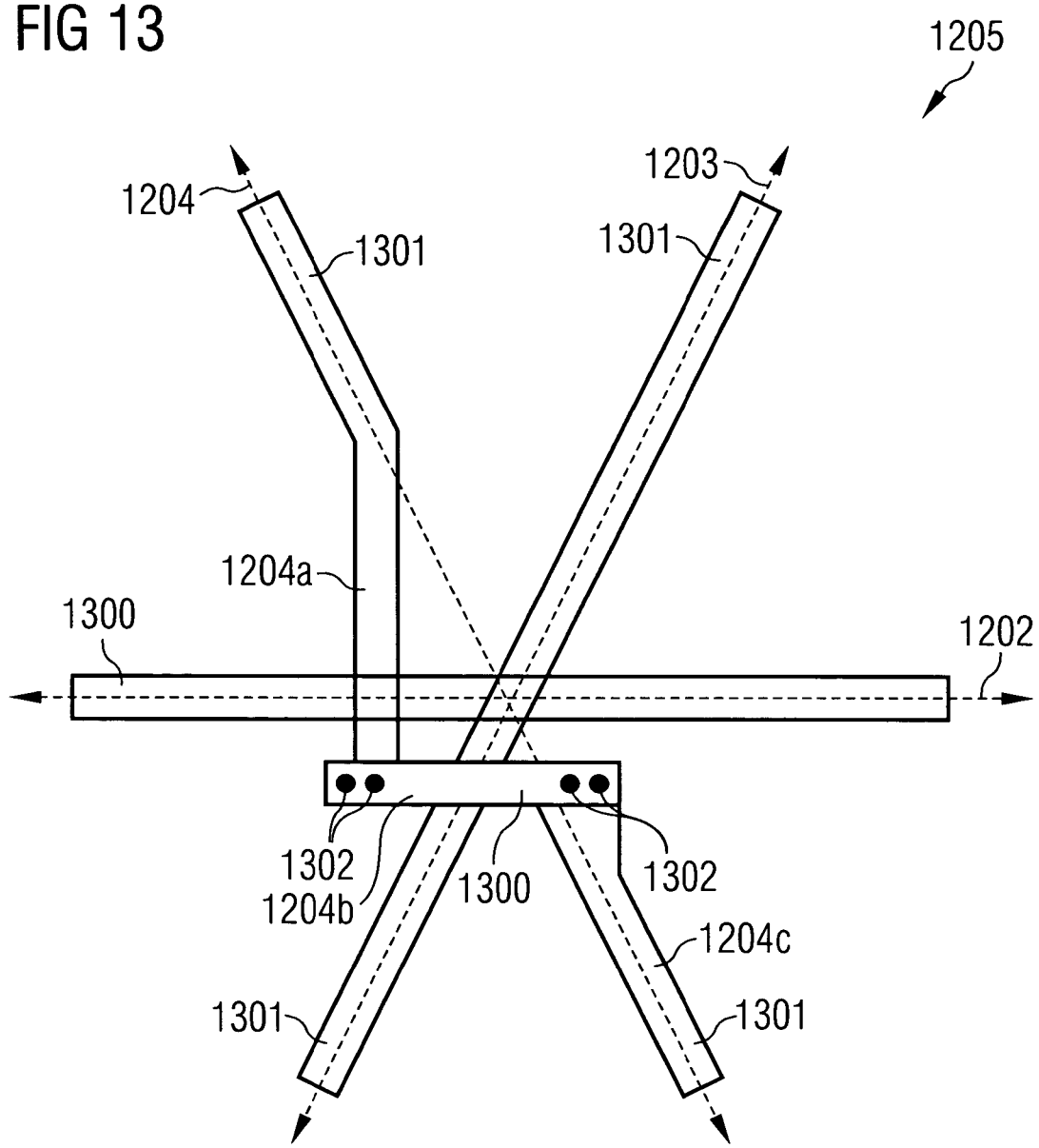
FIG. 13 shows a schematic plan view of a crossover region of three signal lines in accordance with the biosensor array shown in FIG. 12.

For this purpose, FIG. 13 shows a first metallization plane 1300 and a second metallization plane 1301 in plan view. The first metallization plane 1300 is displaced relative to the second metallization plane 1301 in a direction perpendicular to the paper plane of FIG. 13, that is to say that the paper plane of FIG. 13 is parallel to the surface of the biosensor array 1200. One of the first signal lines 1202, which is provided completely in the first metallization plane 1300, one of the second signal lines 1203, which is provided completely in the second metallization plane 1301, and one of the third signal lines 1204, part of which is provided in the first metallization plane 1300 and another part of which is provided in the second metallization plane 1301, as shown in FIG. 13, meet in the crossover region 1205. In order to enable the signal lines 1202 to 1204 to be electrically insulated from one another in the crossover region 1205, the third signal line 1204 in FIG. 13 is divided into a first section 1204a, a second section 1204b and a third section 1204c. The first and the third section 1204a, 1204c run in the second metallization plane 1301, whereas the second section 1204b runs in the first metallization plane 1300. By means of vertical contact-connection elements 1302 arranged in a manner running perpendicular to the paper plane of FIG. 13, the first section 1204a is coupled to the second section 1204b and the second section 1204b is coupled to the third section 1204c of the third signal line 1204. This makes it possible, using just two metallization planes, for three signal lines 1202 to 1204 to cross one another without the electrical insulation being interrupted.

In this connection, it should be noted that a matrix-type arrangement with three (or more) wiring directions need not necessarily be realized with three (or more) independent wiring planes. Two wiring planes are sufficient in any case, as shown schematically in FIG. 13.

A description is given below, referring to FIG. 14, of a redox recycling biosensor array 2200 in accordance with a sixth exemplary embodiment of the invention.

The redox recycling biosensor array 2200 has a silicon substrate 2201 and four redox recycling biosensor zones 2202 arranged in matrix form on the silicon substrate 2201, each of which redox recycling biosensor zones 2202 has a first terminal 2203 and a second terminal 2204. Furthermore, two first signal lines 2205 and two second signal lines 2206 are provided, the first signal lines 2205 being electrically insulated from the second signal lines 2206. In each case the first terminal 2203 of each redox recycling biosensor zone 2202 is coupled to precisely one of the at least one first signal line 2205 and the second terminal 2204 of each redox recycling biosensor zone 2202 is coupled to precisely one of the at least one second signal line 2206. As is shown in FIG. 14, each of the first signal lines 2205 is coupled to two of the redox recycling biosensor zones 2202, and each second signal line 2206 is coupled to likewise two of the redox recycling biosensor zones 2202. Furthermore, provision is made of a first drive unit 2207 for providing a first electrical drive signal and a second drive unit 2208 for providing a second electrical drive signal. Moreover, a first detection unit 2209 coupled to the first drive unit 2207 and a second detection unit 2210 coupled to the second drive unit 2208 are provided, which are set up in such a way that they detect a first and second electrical detection signal of a selected biosensor zone resulting from the first and the second drive signal. Furthermore, a selection unit 2211 is provided, which is set up in such a way that it couples the first drive unit 2207 to the first signal line 2205 of a redox recycling biosensor zone 2202a to be selected and the second drive unit 2208 to the second signal line 2206 of the redox recycling biosensor zone 2202a to be selected, whereby the redox recycling biosensor zone 2202a is selected. By means of the selection unit 2211, which is symbolized schematically in FIG. 14 by a first switching device 2211a and a second switching device 2211b, in accordance with the exemplary embodiment described, in each case precisely one of the redox recycling biosensor zones 2202 is selected. For this purpose, by means of the selection unit 2211, the biosensor zone to be selected, the redox recycling biosensor zone 2202a in accordance with the scenario shown in FIG. 14, is coupled to the first drive unit 2207 and to the second drive unit 2208 in such a way that a first electrical drive signal is applied to the selected redox recycling biosensor zone 2202a by means of the first drive unit 2207, and that a second drive signal is applied to the selected redox recycling biosensor zone 2202a by means of the second drive unit. The first switching device 2211a has an associated switch for each first signal line 2205, which switch can be switched between two positions, in accordance with a first switch position the associated first signal line being coupled to the first drive unit 2209, and in accordance with a second switch position the respective first signal line 2205 being connected to electrical ground potential 2212. The second switching device 2211b analogously has a switch for each second row line 2206, which switch may be present in one of two possible switch positions. In accordance with a first switch position, the associated second signal line 2206 is coupled to the second drive unit 2208 and, in accordance with a second switch position, the respective second signal line 2206 is connected to electrical ground potential 2212. In accordance with the scenario shown in FIG. 14, only the left-hand lower redox recycling biosensor zone 2202 in accordance with FIG. 14 is selected since, in accordance with the switch positions of FIG. 14, only this sensor zone is coupled to the first drive unit 2207 at the first terminal 2203 and to the second drive unit 2208 at the second terminal 2204. By means of the first drive unit 2207, a positive electrical voltage is applied to the first terminal 2203 of the selected redox recycling biosensor zone 2202a, and, by means of the second drive unit 2208, a negative electrical voltage is applied to the second terminal 2204 of the selected redox recycling biosensor zone 2202a. Therefore, the potential difference between the two terminals 2203, 2204 is greater in the case of the selected redox recycling biosensor zone 2202a than in the case of the three nonselected redox recycling biosensor zones 2202. In the case of the latter, in each case one of the terminals 2203, 2204 is at electrical ground potential 2212, and the other terminal 2204, 2203 is either at the positive electrical potential provided by the first drive unit 2207 or at the negative electrical potential provided by the second drive unit 2208. Therefore, it is only in the case of the selected redox recycling biosensor zone 2202a that the potential difference between the two terminals 2203, 2204 suffices to generate electrochemical redox recycling processes to a sufficient extent in the case of a hybridization event at the selected redox recycling biosensor zone 2202a.

A description is given below, referring to FIG. 15A to FIG. 15C, of the configuration of one of the redox recycling biosensor zones 2202, 2202a using the example of the selected redox recycling biosensor zone 2202a.

FIG. 15A shows the selected redox recycling biosensor zone 2202a with a first electrode 2300 and a second electrode 2301, which are integrated in the silicon substrate 2201. A holding region 2302 made of gold material is applied on the first electrode 2300. The holding region 2302 serves for immobilizing DNA probe molecules 2303 as capture molecules on the first electrode 2300. Such a holding region is not provided on the second electrode 2301.

If the redox recycling biosensor zone 2202a is intended to be used to detect DNA strands 2304 having a base sequence that is complementary to the sequence of the immobilized DNA probe molecules 2303, then the redox recycling biosensor zone 2202a is brought into contact with a solution to be examined, namely an electrolyte 2305, in such a way that DNA strands 2304 having a sequence that is complementary to the sequence of the DNA probe molecules 2303, which DNA strands 2304 are possibly contained in the solution 2305 to be examined, can hybridize with the DNA probe molecules 2303.

FIG. 15B shows a scenario in which the solution 2305 to be examined contains DNA strands 2304 to be detected, one of which has hybridized with a DNA probe molecule 2303. The DNA strands 2304 in the solution to be examined are marked with an enzyme label 2306, which makes it possible for molecules described below to be cleaved into electrochemically activated partial molecules. It is customary to provide a considerably larger number of DNA probe molecules 2303 than DNA strands 2304 to be detected that are contained in the solution 2305 to be examined.

Once the DNA strands 2304 contained in the solution 2305 to be examined together with the enzyme label 2306 have hybridized with the immobilized DNA probe molecules 2303, the redox recycling biosensor zone 2202a is preferably specially rinsed. DNA molecules that have not hybridized with capture molecules can be removed in the course of rinsing. The rinsing solution used for rinsing is admixed with an electrochemically inactive substance containing molecules which can be cleaved by means of the enzyme 2306 into two partial molecules 2308, at least one of which is electrochemically active and usually has an electrical charge.

As is shown in FIG. 15C, the partial molecules 2308 that are negatively charged in accordance with the exemplary embodiment described are attracted to the positively charged electrode 2300, which is indicated by means of an arrow 2309. The negatively charged partial molecules 2308 are oxidized at the first electrode 2300, to which a positive electrical potential is applied via the first terminal 2203 by means of the first drive unit 2207, and are attracted as oxidized partial molecules 2310 to the negatively charged second electrode 2301, to which a negative electrical potential is applied via the second terminal 2204 by means of the second drive unit 2208. They are reduced again there. The reduced partial molecules 2311 migrate again to the positively charged first electrode 2300. In this way, an electric circulating current is generated which is proportional to the number of charge carriers respectively generated by means of the enzymes 2306.

What is essential for the functionality of the selected redox recycling biosensor zone 2202a is that one of the electrodes 2300 is positively charged to a sufficiently great extent with respect to one of the other electrodes 2301, so that the reduction and oxidation processes can proceed. For this reason, the nonselected redox recycling biosensor zones 2202 from FIG. 14, in accordance with the operating state shown, are unable to generate sufficiently strong currents that can be detected by the detection units 2211, 2209 even if a sensor event has taken place at them.

One example of a chemical system suitable for redox recycling is the use of a salt solution as buffer solution, an alkaline phosphatase as label molecule 2306 and para-aminophenol phosphate as electrochemically inactive substance 2307. The subspecies to be oxidized that is generated by means of the label may be para-aminophenol and the subspecies to be reduced that is generated by means of the label may be quinoneimine.

A description is given below, referring to FIG. 16, of a biosensor array 2400 in accordance with a seventh exemplary embodiment of the invention.

In the case of the biosensor array 2400, a multiplicity of redox recycling biosensor zones 2202 are arranged in matrix form on a silicone substrate 2201. The biosensor array 2400 has n rows and m columns of redox recycling biosensor zones 2202 arranged in matrix form. Furthermore, as is shown in FIG. 16, m first signals lines 2205 and n second signal lines 2206 are provided, that is to say n+m signal lines. A redox recycling biosensor zone 2202 configured as an interdigital electrode arrangement is in each case arranged in the crossover region between a respective first signal line 2205 and a respective second signal line 2206. Said redox recycling biosensor zone 2202 contains two interdigitated interdigital electrodes 2401, 2402 that are configured in a manner similar to the interdigital electrodes 112, 113 shown in FIG. 1C.

The first drive unit 2207 has a first DC voltage source Vg 2403 and a further terminal, at which an electrical ground potential 2212 is provided. The first switching device 2211a has m first switches 2404, each of which is coupled to one of the first signal lines 2205. A column of redox recycling biosensor zones is selected by virtue of the redox recycling biosensor zones of the column being coupled to the first DC voltage source Vg 2403. All the other columns of the redox recycling biosensor zones 2202 are coupled to the electrical ground potential 2212 on account of correspondingly chosen switch positions of the first switches 2404, as shown in FIG. 16. In accordance with the scenario shown in FIG. 16, only the redox recycling biosensor zones 2202 in the second column from the left are coupled to the first DC voltage source Vg 2403.

Figure 16:
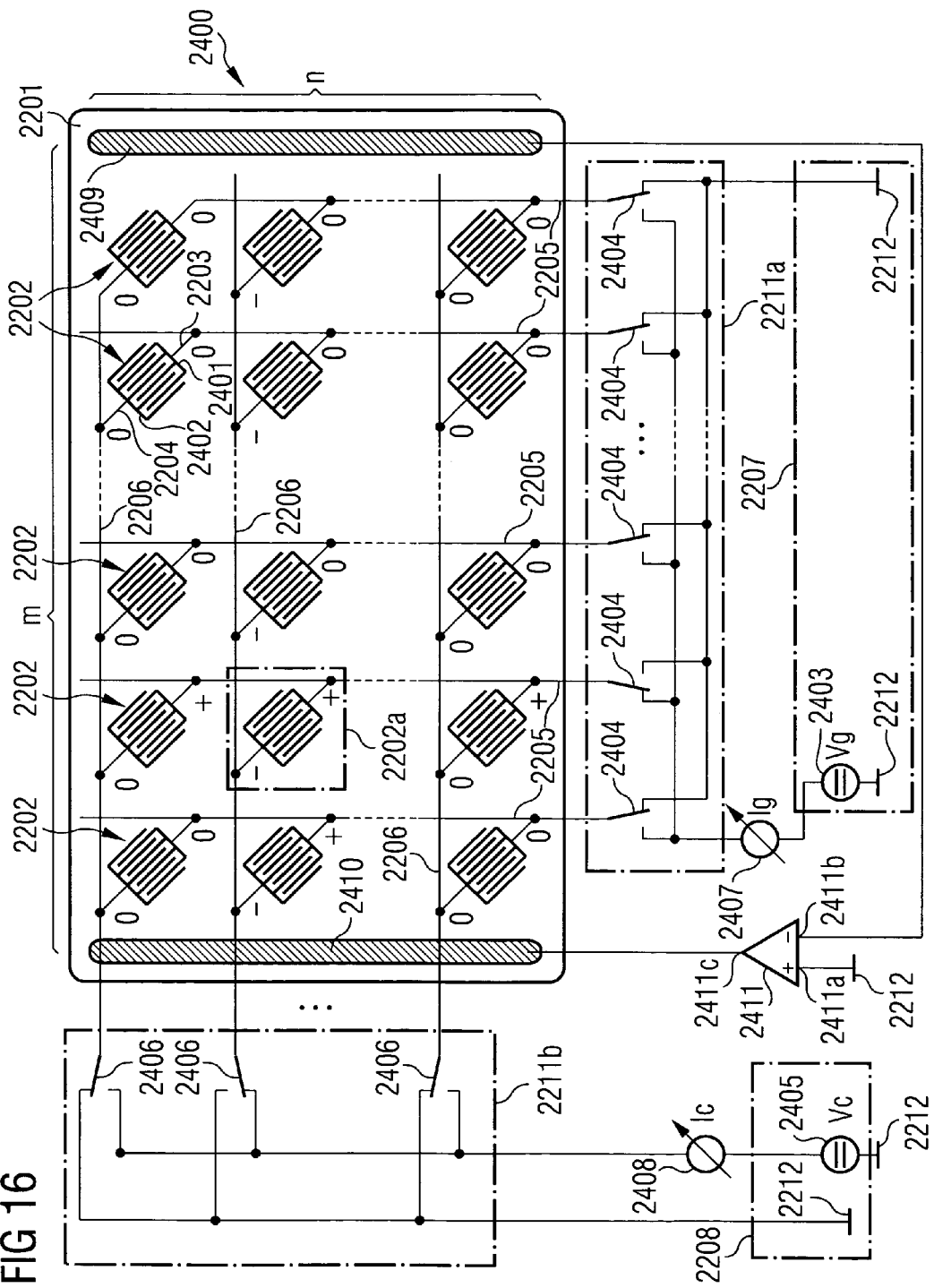
FIG. 16 shows a biosensor array in accordance with a seventh exemplary embodiment of the invention.

A row of redox recycling biosensor zones 2202 is selected by virtue of the row to be selected, the second row from the top in accordance with the scenario shown in FIG. 16, being coupled to a second DC voltage source Vc 2405 of the second drive unit 2208. This is effected by means of a suitable choice of the switch positions of second switches 2406 of the second switching device 2211b. Furthermore, the second drive unit contains a terminal that provides the electrical ground potential 2212.

The first detection unit is realized as a first current detecting unit Ig 2407 for detecting an electric current of a selected column line 2205, and the second detection unit is realized as a second current detecting unit Ic 2408 that can be used to detect an electric current flowing on a selected row.

Furthermore, the biosensor array 2400 has a potentiostat device. This is constructed from a reference electrode 2409 on the substrate 2201, a counterelectrode 2410 on the substrate 2201 and an operational amplifier 2411 arranged outside the chip ("off-chip"). A noninverting input 2411a of the operational amplifier 2411 is at an electrical ground potential 2212. An inverting input 2411b of the operational amplifier 2411 is coupled to the counterelectrode 2410. These components together form a potentiostat circuit. The latter may advantageously be utilized for allocating to an analyte that is introduced into the biosensor array 2400 a stable electrochemical potential in a low-resistance fashion. This configuration with a potentiostat device is advantageous particularly when the biosensor zones are set up as redox recycling biosensor zones.

In the case of the biosensor array 2400, the first drive lines 2205 and the second drive lines 2206 are formed in different planes, thereby enabling electrically insulated line crossovers. All m columns may optionally be coupled to the first DC voltage source Vg 2403 or to electrical ground potential 2212. All n rows may optionally be coupled to the second DC voltage source Vc 2405 or to the electrical ground potential 2212. The current detecting instruments Ig 2407 and Ic 2408 can be used to measure the electric currents flowing through the associated DC voltage sources 2403, 2405. Generator and collector current can thus be characterized in the specified configuration. Since these currents are approximately identical in terms of magnitude, it is optionally possible also for only one of the currents to be measured. The detection of one current is sufficient and represents a realization with a minimal outlay. The detection of both currents enables a redundant detection of a sensor event and therefore an increased detection sensitivity and robustness against errors.

For read-out operation, the positive voltage Vg is applied to precisely one column and the negative voltage Vc is applied to precisely one row. The electrical ground potential 2212 is present at all the other rows and columns. As depicted by "+" and "−" symbols in FIG. 16, it is only at the redox recycling biosensor zone 2202a lying in the crossover region between the selected row 2206 and the selected column 2205 that a sufficiently large potential gradient is present to permit the processes of both oxidation and reduction. At all the other redox recycling biosensor zones 2202, the magnitude of the voltage at at least one of the terminals 2203, 2204 is less than the threshold value which must be exceeded in order to initiate both desired electrochemical processes. If appropriate, when the voltages are applied, a single brief current surge may occur here at one of the electrodes 2401 or 2402, but it decays rapidly, and is not a continuously rising current as in the case of the selected redox recycling biosensor zone 2202a. The electrical ground potential 2212 is present at both terminals 2203, 2204 at most of the redox recycling biosensor zones 2202 of the matrix.

A description is given below, referring to FIG. 17, of a biosensor array 2500 in accordance with an eighth exemplary embodiment of the invention.

In the case of redox recycling biosensor zones, generator and collector current, i.e. Ig and Ic, are often very similar in terms of magnitude, but have a different sign. Consequently, it suffices in principle to measure and evaluate only one of the two currents. An exemplary embodiment of the biosensor array according to the invention which is based on this fact is shown in FIG. 17.

In the case of the biosensor array 2500, the voltage Vg is applied to all the column lines 2205 by means of the first DC voltage source Vg 2403. Furthermore, the voltage Vg of the first DC voltage source Vg 2403 is applied to all but one of the row lines 2206. It is only at the second row from the top in accordance with FIG. 17 that a coupling between the associated second signal line 2206 and the second DC voltage source Vc 2405 is produced on account of the switch positions of the second switches 2406. Consequently, the potential difference zero is present at all the redox recycling biosensor zones 2202 apart from the redox recycling biosensor zones 2202 in the selected second row 2501. The requirement made of the applied voltages for the occurrence of oxidation and reduction processes is satisfied for all the redox recycling biosensor zones 2202 of the selected row 2501. That is to say that all the redox recycling biosensor zones of the selected row 2501 can supply electric current if sensor events take place at them. However, since only the electric current of the second column of redox recycling biosensor zones 2202 in accordance with FIG. 16 is measured on account of the switch positions of the first switches 2404, only the electric current of the selected redox recycling biosensor zone 2202a is detected in accordance with the scenario shown in FIG. 17. In this way, each of the redox recycling biosensor zones 2202 within the matrix can be separately selected selectively by means of setting suitable switch positions 2404, 2406.

As an alternative, the functions of rows and columns can be interchanged, and so can the roles of Vg and Vc, that is to say that the value Ic is then detected instead of the value Ig.

Figure 18:
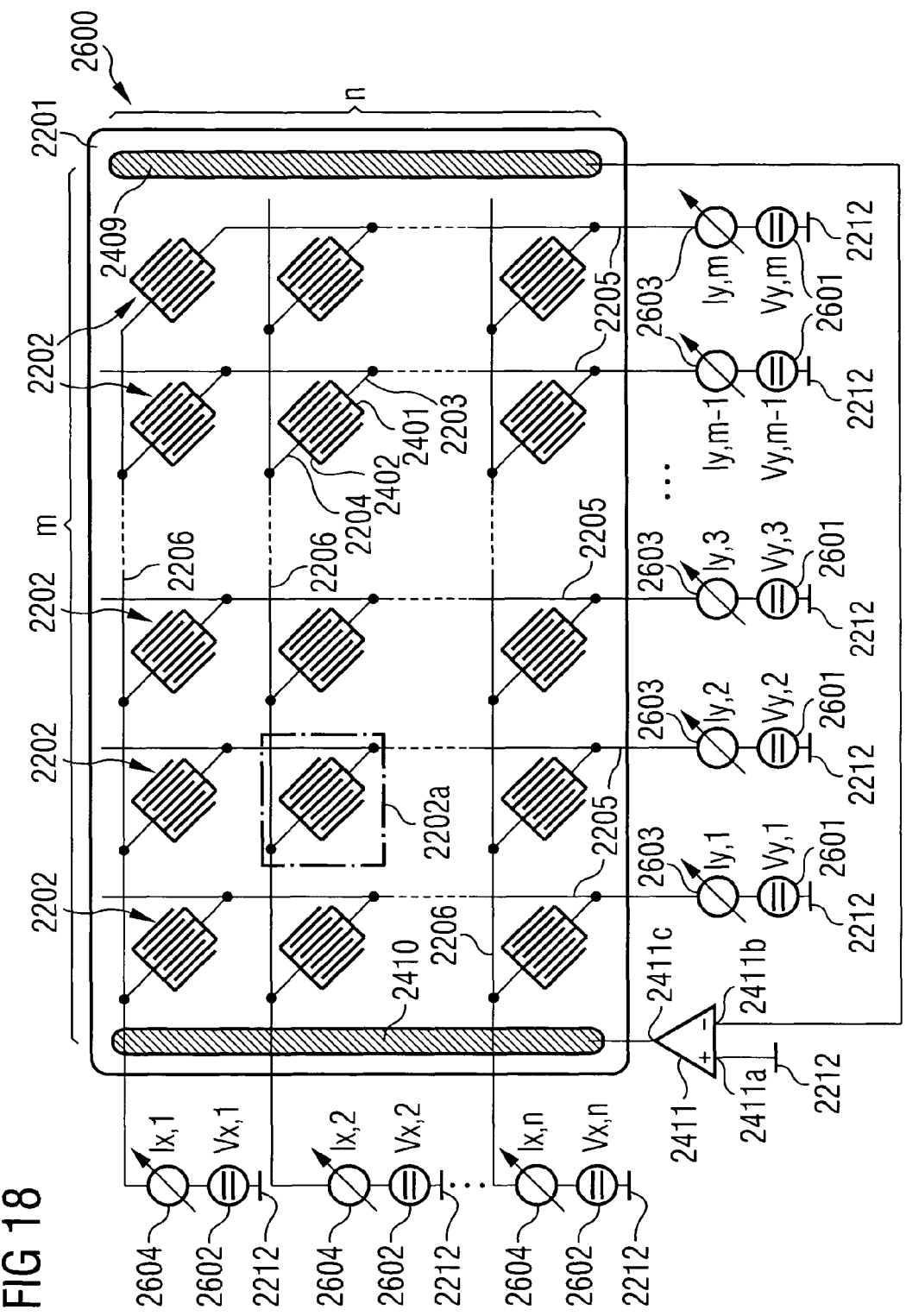
FIG. 18 shows a biosensor array in accordance with a ninth exemplary embodiment of the invention.

A description is given below, referring to FIG. 18, of a biosensor array 2600 in accordance with the ninth exemplary embodiment of the invention.

In the case of the biosensor array 2600, a separate first DC voltage 2601 Vy, i, where i=1, 2, ..., m, and also a first current detecting device 2603 Iy, i where i=1, 2, ..., m, are provided for each first signal line 2205, that is to say for each column of redox recycling biosensor zones 2202. Furthermore, in each case a separate second DC voltage source 2602 Vx, j where j=1, 2, ..., n, and a separate second current detecting device 2604 Ix, j where j=1, 2, ..., n are provided for each second signal line 2206, that is to say for each row of redox recycling biosensor zones 2202. Clearly, each column and each row are provided with a separate voltage source and with a separate current measuring instrument. Depending on the allocation of voltages to the voltage sources shown, the operation of the sensor arrangement from FIG. 16 and from FIG. 17 can be achieved with this configuration. One advantage of the biosensor array 2600 is that row-wise or column-wise parallel read-out is possible. Clearly, in the case of the exemplary embodiment shown in FIG. 18, the selection unit is integrated in the control of the DC voltage sources 2601 and 2602 since each of the voltage sources can optionally be connected in and disconnected.

Figure 19:
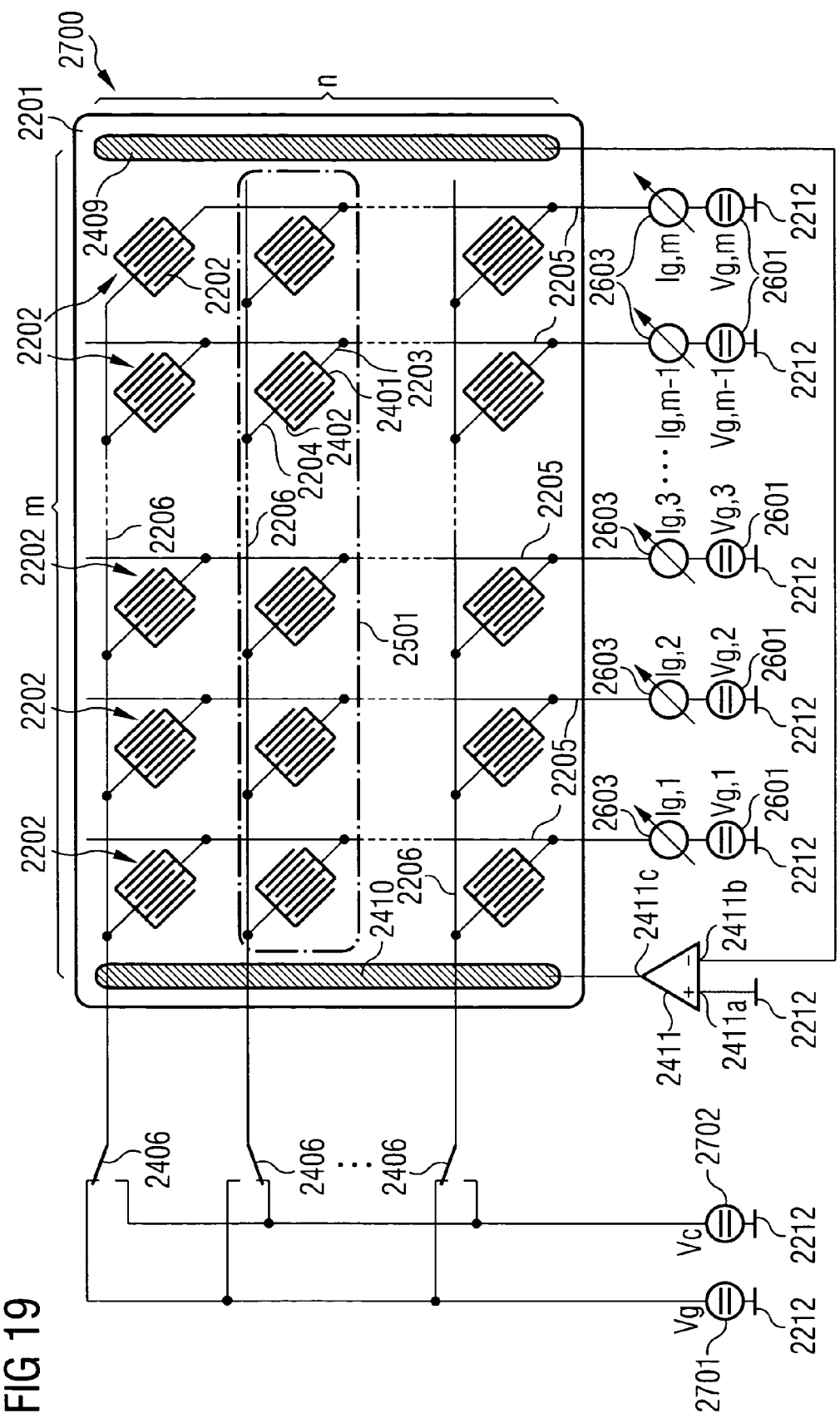
FIG. 19 shows a biosensor array in accordance with a tenth exemplary embodiment of the invention.

A description is given below, referring to FIG. 19, of a biosensor array 2700 in accordance with a tenth exemplary embodiment of the invention.

In the case of the biosensor array 2700, each column of redox recycling biosensor zones 2202, that is to say each first signal line 2205, is coupled to a separate first DC voltage source 2601 and to a separate first current detecting device 2603. By contrast, in each case a common third DC voltage source Vg 2701 and fourth DC voltage source Vc 2702 are provided for the different rows of redox recycling biosensor zones 2202, precisely one row of redox recycling biosensor zones being coupled to the fourth DC voltage source Vc 2702 by means of the second switches 2406, whereas all the other rows are coupled to the third DC voltage source Vg 2701. In accordance with the exemplary embodiment shown in FIG. 19, only the selected row 2501 is coupled to the fourth DC voltage source Vc 2702. In accordance with the scenario shown, all the first DC voltage sources 2601 supply the electrical potential Vg, so that it is only at the redox recycling biosensor zones 2202 of the selected row 2501 that a potential difference is present which is large enough that redox recycling processes can occur to a sufficient extent. These sensor signals are read out row-wise by virtue by of each of the first current detecting devices 2603 detecting the electric current of precisely one assigned redox recycling biosensor zone of the selected row 2501.

In accordance with a similar principle, read-out may also be effected columnwise in each case.

Figure 20:
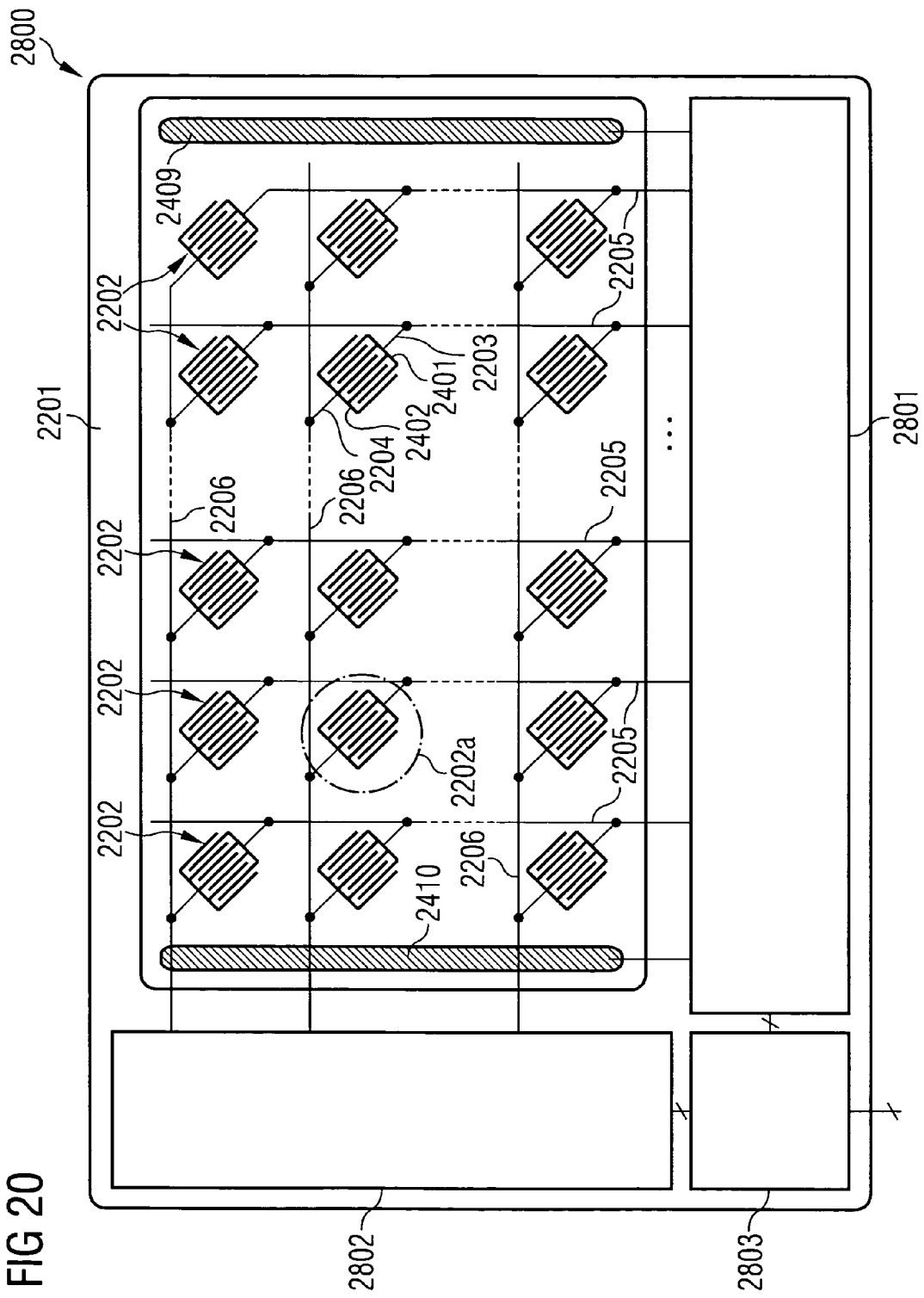
FIG. 20 shows a biosensor array in accordance with an eleventh exemplary embodiment of the invention.

A description is given below, referring to FIG. 20, of a biosensor array 2800 in accordance with an eleventh exemplary embodiment of the invention.

The biosensor array 2800 has a first circuit block 2801 and a second circuit block 2802, and also an input/output interface 2803 coupled to the two circuit blocks 2801, 2802. A sensor signal, for example an electrical drive signal or an electrical detection signal, may be provided at the input/out interface 2803.

The biosensor array 2800 represents a so-called "active" chip. This is understood to mean a semiconductor substrate in which circuits that may have different functions are monolithically integrated. In particular, the components voltage sources 2403 and 2601, current detecting units 2407 and 2603, operational amplifiers 2411 and parts of the selection unit 2211 are integrated in the first circuit block 2801, and other components such as the second voltage sources 2405 and 2602, current detecting devices 2408 and 2604, other parts of the selection unit 2211, etc. are integrated in the second circuit block 2802. Furthermore, further components for the signal preprocessing and the signal further processing are realized "on-chip" in the circuit blocks 2801, 2802. Moreover, the chip of the biosensor array 2800 has a defined (e.g. digital) interface 2803 (I/O) configured in accordance with the requirements of the respective application.

The use of the architecture according to the invention on active chips may be advantageous for example if use is made of a large number of relatively small-area interdigital structures whose area no longer permits an active circuit for controlling the respective sensor to be realized beneath each sensor. Furthermore, particular advantages are afforded if the requirements made of the performance of the circuits realized ("on-chip") are very high. This last is applicable particularly when the area of a sensor element has a crucial influence on the performance (for example the noise).

Figure 21:
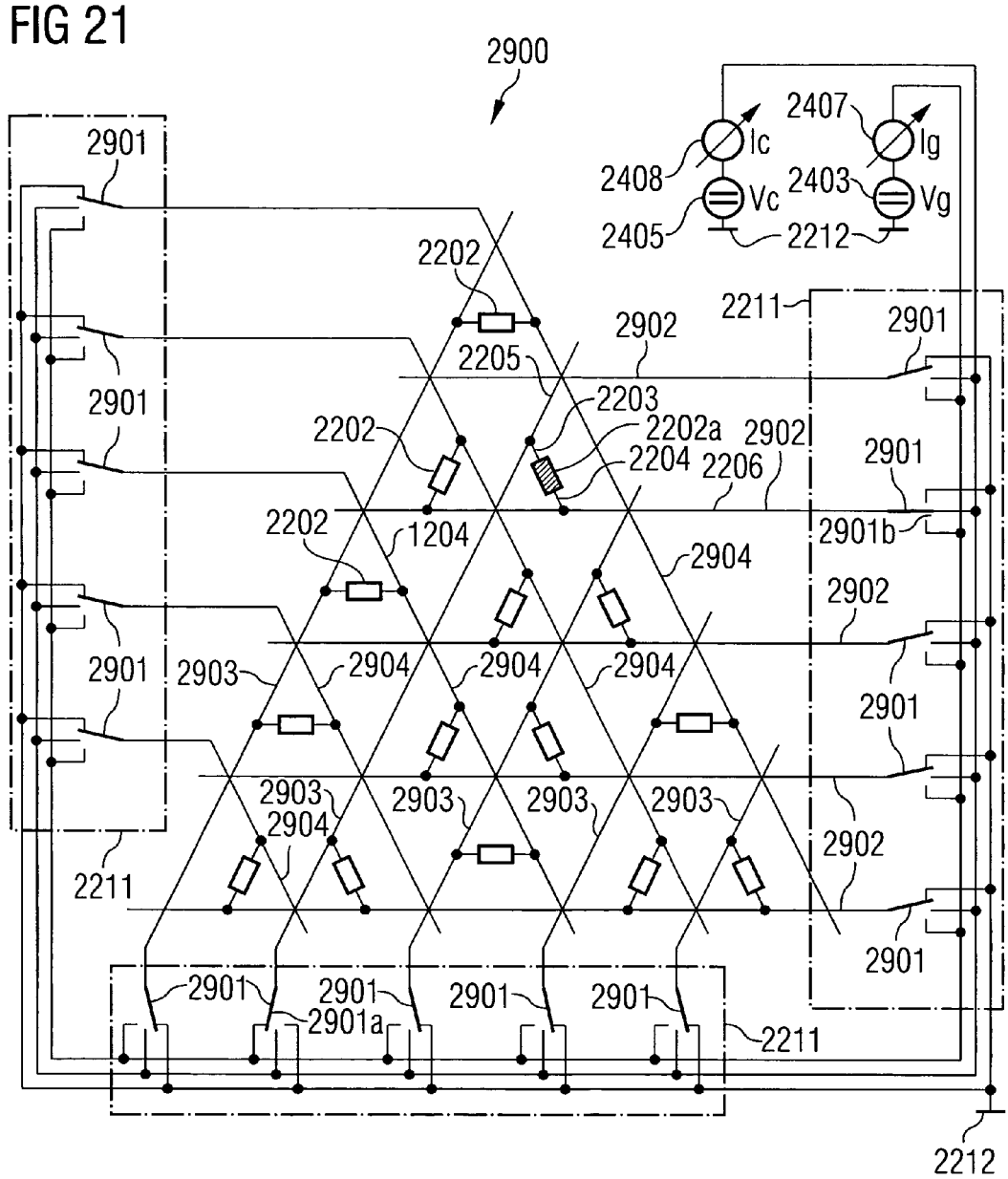
FIG. 21 shows a biosensor array in accordance with a twelfth exemplary embodiment of the invention.

A description is given below, referring to FIG. 21, of a biosensor array 2900 in accordance with a twelfth exemplary embodiment of the invention.

The biosensor array 2900 is an arrangement of redox recycling biosensor zones 2202 which are provided as a triangular matrix with three wiring directions. Furthermore, a common first DC voltage source 2403 Vg is provided as a first drive unit and a common first current detecting device 2407 Ig is provided as a first detection unit. Moreover, provision is made of a second DC voltage source 2405 Vc and a second current detecting unit 2408 Ic—coupled thereto—as a second detection unit. The selection unit 2211 is symbolized by means of a multiplicity of switches 2901 with controllable switch positions. The switch positions are controllable by means of the selection unit 2211. Furthermore, in FIG. 21, first lines 2902, second lines 2903 and third lines 2904 are arranged such that they run in such a way that, in crossover regions (electrically insulated from one another) of the lines 2902 to 2904, the latter cross one another at angles of 60°. In particular, FIG. 21 shows a selected redox recycling biosensor zone 2202a, which is selected on account of the switch positions of the switches 2901 as shown in FIG. 21. A first switch 2901a is in a switch position such that the first terminal 2203 of the selected redox recycling biosensor zone 2202a is coupled to the first DC voltage source 2403 Vg and to the first current detecting device 2407 Ig. Furthermore, a second switch 2901b is in a switch position such that the second terminal 2204 of the selected redox recycling biosensor zone 2202a is coupled to the second DC voltage source Vc 2405 and to the second current detecting unit 2408 Ic. The switch positions of all the other switches 2901 are in a position such that the first, second and third signal lines 2902 to 2904 adjoining said switches 2901 are at electrical ground potential 2212. In other words, in accordance with the scenario shown in FIG. 21, the selected redox recycling biosensor zone 2202a is the only one of the redox recycling biosensor zones 2202 which is coupled both to the DC voltage source 2403 Vg and to the DC voltage source 2405 Vc. In accordance with the scenario shown in FIG. 21, the first line 2902 connected to the selected redox recycling biosensor zone 2202a functions as second signal line 2206, whereas the second line 2903 connected to the selected redox recycling biosensor zone 2202a functions as first signal line 2205. Each of the switches 2901 has three switch positions, so that the respectively associated lines 2902 to 2904 can optionally be coupled to the electrical ground potential 2212, the DC voltage source Vg 2403 or the DC voltage source Vc 2405. As a result, an independent measurement is possible on each position of the sensor array 2900. The configuration of FIG. 21 corresponds to the configuration of FIG. 16 but in an architecture with a triangular matrix.

Figure 22:
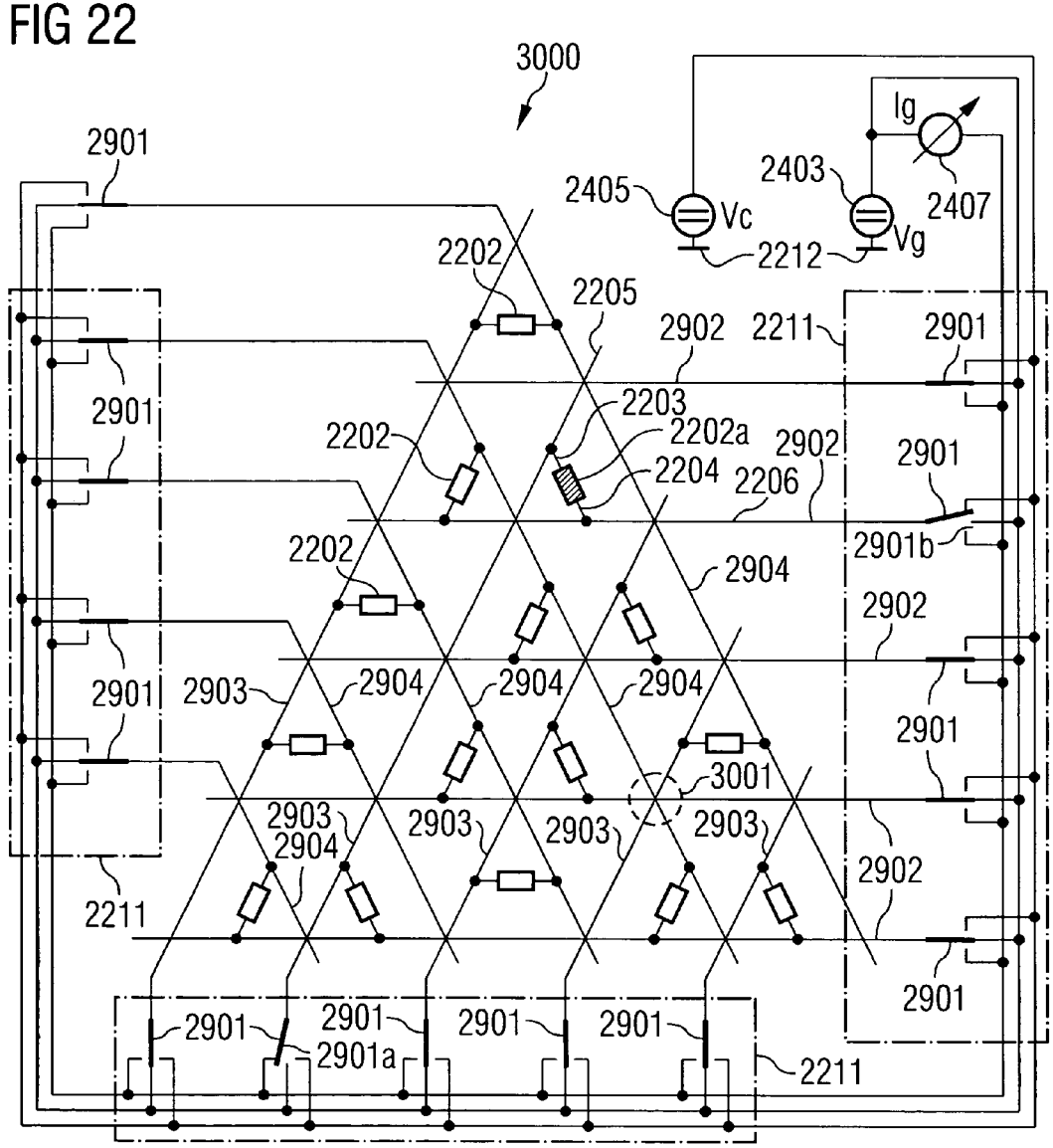
FIG. 22 shows a biosensor array in accordance with a thirteenth exemplary embodiment of the invention.

A description is given below, referring to FIG. 22, of a biosensor array 3000 in accordance with a thirteenth exemplary embodiment of the invention.

Figure 17:
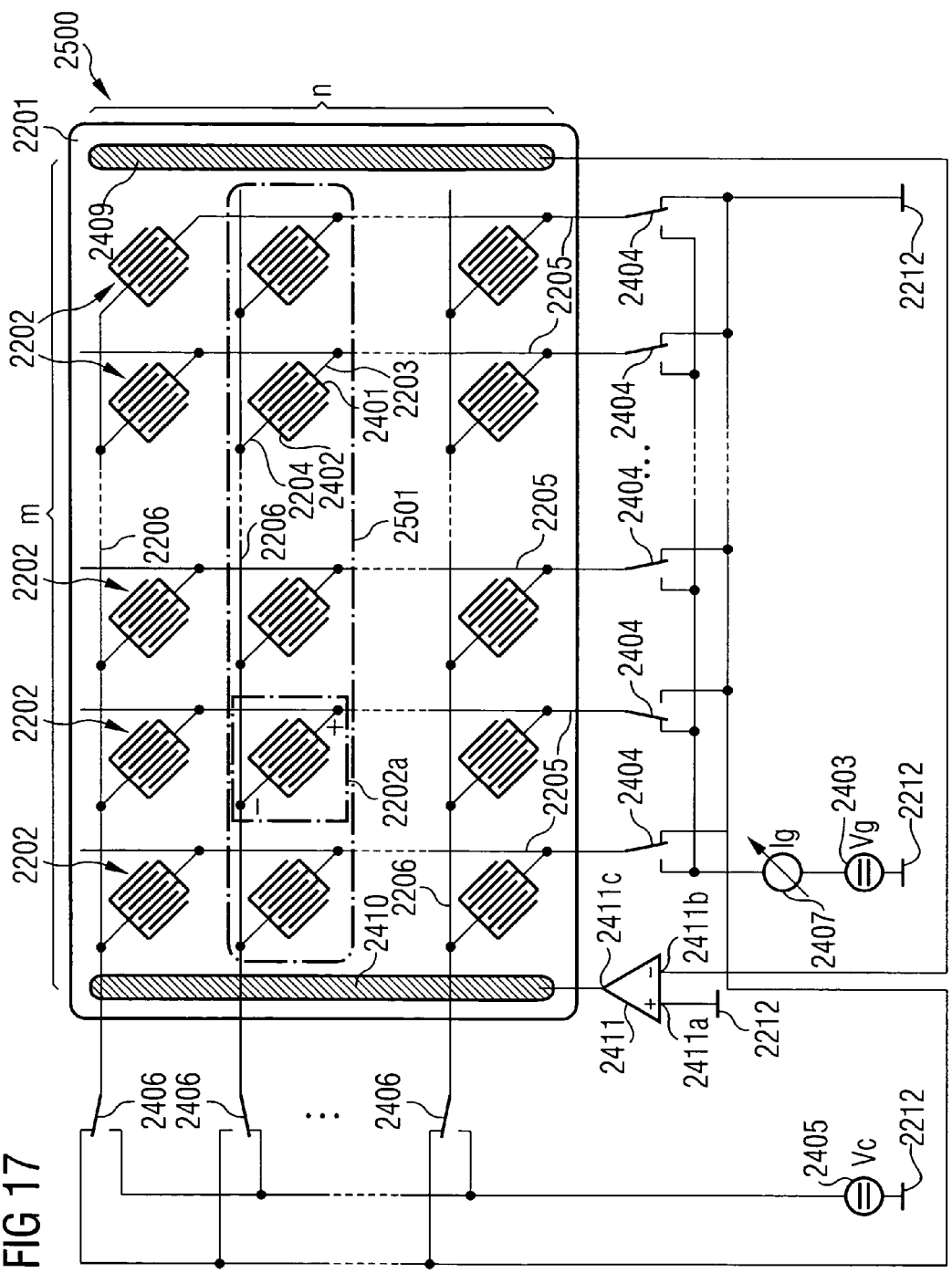
FIG. 17 shows a biosensor array in accordance with an eighth exemplary embodiment of the invention.

The biosensor array 3000 corresponds to the configuration of FIG. 17, but is embodied in an architecture with a triangular-matrix-type arrangement of the redox recycling biosensor zones 2202. In accordance with the scenario illustrated in FIG. 22, the first switch 2901a is in a switch position such that the associated second line 2903 is coupled to the current detecting unit 2407 Ig. Furthermore, the second switch 2901b is in a position such that the associated first line 2902 is the only one coupled to the second DC voltage source Vc 2405. All the other switches of the switches 2901 are in a position such that the associated lines 2902 to 2904 are coupled to the first voltage source 2403 Vg. As a result, the potential difference Vg–Vc is applied between the terminals 2203, 2204 of the selected redox recycling biosensor zone 2202a, and the current flowing on the first signal line 2205 is detected by means of the first current detecting unit 2407.

A description is given below, referring to FIG. 23, of how a crossover region 3001 between one of the first lines 2902, one of the second lines 2903 and one of the third lines 2904 can be realized using only two wiring planes.

Figure 23:
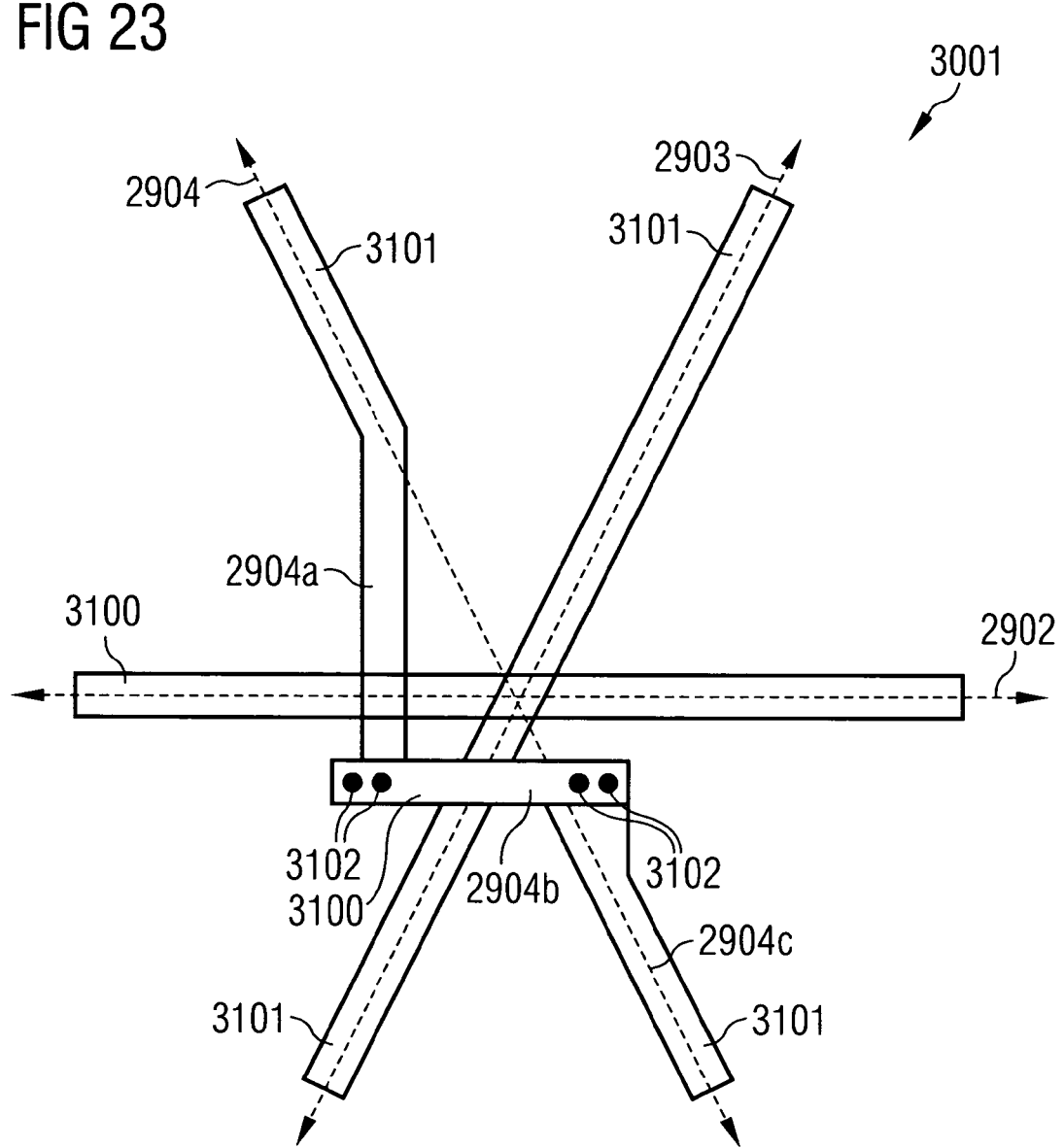
FIG. 23 shows a schematic plan view of a crossover region of three signal lines in accordance with the biosensor array shown in FIG. 22.

FIG. 23 shows a first metallization plane 3100 and a second metallization plane 3101 in plan view. The first metallization plane 3100 is displaced relative to the second metallization plane 3101 in a direction perpendicular to the paper plane of FIG. 23, that is to say that the paper plane of FIG. 23 is parallel to the surface of the biosensor array 2900. One of the first lines 2902, which is provided completely in the first metallization plane 3100, one of the second signal lines 2903, which is provided completely in the second metallization plane 3101, and one of the third lines 2904, part of which is provided in the first metallization plane 3100 and another part of which is provided in the second metallization plane 3101, as shown in FIG. 23, meet in the crossover region 3101. In order to enable the signal lines 2902 to 2904 to be electrically insulated from one another in the crossover region 3001, the third line 2904 in FIG. 23 is divided into a first section 2904a, a second section 2904b and a third section 2904c. The first section 2904a and the third section 2904c run in the second metallization plane 3101, whereas the second section 2904b runs in the first metallization plane 3100. By means of vertical contact-connection elements 3102 arranged in a manner running perpendicular to the paper plane of FIG. 23, the first section 2904a is coupled to the second section 2904b and the second section 2904b is coupled to the third section 2904c of the third line 2904. This makes it possible, using only two metallization planes, for three lines 2902 to 2904 to cross one another without the electrical insulation being interrupted.

In this connection, it should be noted that a matrix-type arrangement with three (or more) wiring directions need not necessarily be realized with three (or more) independent wiring planes. Two wiring planes are sufficient in any case, as shown schematically in FIG. 23.

The invention claimed is:

1. A method for operating a biosensor array having a substrate, a plurality of biosensor zones arranged on the substrate and comprising a first sensor electrode and a second sensor electrode, each of which biosensor zones has a first terminal and a second terminal, wherein the first terminal is directly connected to the first sensor electrode and the second terminal is directly connected to the second sensor electrode, at least one drive line and at least one detection line, the at least one drive line being electrically insulated from the at least one detection line, wherein in each case the first terminal of each biosensor zone is coupled to precisely one of the at least one drive line and the second terminal of each biosensor zone being coupled to precisely one of the at least one detection line, at least one of the at least one drive line and at least one of the at least one detection line is coupled to at least two of the biosensor zones, a drive unit configured to provide an electrical drive signal, a detection unit configured to detect an electrical detection signal resulting from the electrical drive signal, and a selection unit configured to couple the drive unit to the drive line of a biosensor zone to be selected and the detection unit to the detection line of the biosensor zone to be selected, whereby the biosensor zone is selected, the method comprising:

coupling the drive unit to the drive line of a biosensor zone to be selected and coupling the detection unit to the detection line of the biosensor zone to be selected via the first terminal and the second terminal connected to the biosensor zone including capture molecules immobilized thereon, whereby the biosensor zone including the first sensor electrode and the second sensor electrode is configured such that capture molecules can be immobilized thereon and capture molecules are immobilized on at least one of the first sensor electrode and the second sensor electrode, whereby the biosensor zone is selected;

providing the drive line of the selected biosensor zone with an electrical drive signal; and detecting an electrical detection signal of the selected biosensor zone that results from the electrical drive signal, on the detection line of the selected biosensor zone.

2. The method as claimed in claim 1, wherein, for the at least one selected biosensor zone on the basis of the drive signal and the detection signal, determining at least one of whether sensor events have taken place at the at least one selected biosensor zone and the quantity in which sensor events have taken place at the at least one selected biosensor zone.

3. The method as claimed in claim 1, further comprising selectively activating and deactivating the drive lines using a first switching unit and selectively activating and deactivating the detection lines using a second switching unit.

4. A method for operating a biosensor array having a substrate, a plurality of biosensor zones arranged on the substrate and comprising first sensor electrode and a second sensor electrode, each of which biosensor zones has a first terminal and a second terminal, wherein the first terminal is directly connected to the first sensor electrode and the second terminal is directly connected to the second sensor electrode, at least one first signal line and at least one second signal line, the at least one first signal line being electrically insulated from the at least one second signal line, wherein in each case the first terminal of each biosensor zone is coupled to precisely one of the at least one first signal line and the second terminal of each biosensor zone is coupled to precisely one of the at least one second signal line, at least one of the at least one first signal line and at least one of the at least one second signal line is coupled to at least two of the biosensor zones, a first drive unit configured to provide a first electrical drive signal and a second drive unit configured to provide a second electrical drive signal, at least one of a first detection unit coupled to the first drive unit and a second detection unit coupled to the second drive unit, which detects or detect at least one of a first and a second electrical detection signal of a selected biosensor zone that results from the first and the second electrical drive signal, a selection unit configured to couple the first drive unit to the first signal line of a biosensor zone to be selected and the second drive unit to the second signal line of the biosensor zone to be selected, whereby the biosensor zone is selected, the method comprising:

coupling the first drive unit to the first signal line of a biosensor zone to be selected and coupling the second drive unit to the second signal line of the biosensor zone to be selected via the first terminal and the second terminal connected to the biosensor zone including the first sensor electrode and the second sensor electrode configured such that capture molecules can be immobilized thereon, whereby the biosensor zone is selected;

providing the first signal line of the selected biosensor zone with a first electrical drive signal and providing the second signal line of the selected biosensor zone with a second electrical drive signal; and at least one of detecting a first detection signal resulting from the first and the second electrical drive signals on the first signal line of the selected biosensor zone and detecting a second detection signal resulting from the first and the second electrical drive signals on the second signal line of the selected biosensor zone.

5. The method as claimed in claim 4, wherein, for the at least one selected biosensor zone on the basis of at least one of the first and the second detection signal, determining at least one of whether sensor events have taken place at the at least one selected biosensor zone and the quantity in which sensor events have taken place at the at least one selected biosensor zone.

6. The method as claimed in claim 4, further comprising selectively activating and deactivating the drive lines using a first switching unit and selectively activating and deactivating the detection lines using a second switching unit.

7. A biosensor array comprising:
a substrate;
a plurality of biosensor zones arranged on the substrate, each biosensor zone comprising a first sensor electrode and a second sensor electrode configured such that capture molecules can be immobilized thereon;
capture molecules immobilized on at least one of the first sensor electrode and the second sensor electrode;
a first terminal directly electrically connected to the first sensor electrode and a second terminal directly electrically connected to the second sensor electrode of each biosensor zone;
at least one drive line and at least one detection line, the at least one drive line being electrically insulated from the at least one detection line;
wherein in each case the first terminal of each biosensor zone is coupled to precisely one of the at least one drive line and the second terminal of each biosensor zone is coupled to precisely one of the at least one detection line, the at least one drive line and the at least one detection line being separate lines, and at least one of the at least one drive line and at least one of the at least one detection line is coupled to at least two of the biosensor zones;
a drive unit configured to provide an electrical drive signal;
a detection unit configured to detect an electrical detection signal resulting from the electrical drive signal; and
a selection unit configured to couple the drive unit to the drive line of a biosensor zone to be selected and the detection unit to the detection line of the biosensor zone to be selected, whereby the biosensor zone is selected.

8. The biosensor array as claimed in claim 7, further comprising an evaluation unit configured to determine for the at least one selected biosensor zone on the basis of the drive signal and the detection signal at least one of whether sensor events have taken place at the at least one selected biosensor zone and the quantity in which sensor events have taken place at the at least one selected biosensor zone.

9. The biosensor array as claimed in claim 7, wherein at least one of the biosensor zones is an electrochemical biosensor zone or an impedance biosensor zone.

10. The biosensor array as claimed in claim 9, wherein at least one biosensor zone set up as an electrochemical biosensor zone is a redox recycling biosensor zone.

11. The biosensor array as claimed in claim 7, wherein at least one biosensor zone is an interdigital electrode biosensor zone.

12. The biosensor array as claimed in claim 7, wherein the biosensor zones are grouped to form a plurality of biosensor groups such that each biosensor group can optionally be operated separately from the other biosensor groups or jointly with at least a portion of the other biosensor groups.

13. The biosensor array as claimed in claim 7, wherein the substrate is a ceramic substrate, a semiconductor substrate, a glass substrate, or a plastic substrate.

14. The biosensor array as claimed in claim 7, wherein the electrical drive signal is a temporally variable electrical signal.

15. The biosensor array as claimed in claim 7, wherein the drive signal is a temporally variable electrical voltage and the detection signal is a temporally variable electric current; or
the drive signal is a temporally variable electric current and the detection signal is a temporally variable electrical voltage.

16. The biosensor array as claimed in claim 8, wherein the substrate has integrated therein at least one of the following:

an analog-to-digital converter circuit, which can convert an analog electrical signal into a digital signal and provide the digital signal to the evaluation unit;

an electrical supply unit, which can provide at least one of electrical voltage signals and electric current signals to at least one of the drive unit and the selection unit;

a digital-to-analog converter circuit, which can convert at least one of a digital voltage signal and a current signal of the supply unit into an analog signal and provide the analog signal to at least one of the drive unit and the selection unit;

an input/output interface; and an amplifier unit configured to amplify the electrical detection signal.

17. The biosensor array as claimed in claim 7, wherein the at least one drive line and the at least one detection line are at least partly formed in two different line planes such that they are at least one of in, on, and below the substrate.

18. The biosensor array as claimed in claim 17, wherein the biosensor zones are formed in precisely one of the line planes.

19. The biosensor array as claimed in claim 17, wherein, in a first line section, in which the at least one drive line and the at least one detection line are free of a mutual crossover, the at least one drive line and the at least one detection line are formed such that they run in the same plane, and in which, in a second line section, in which the at least one drive line and the at least one detection line mutually cross one another, the at least one drive line and the at least one detection line are formed such that they run in different planes.

20. The biosensor array as claimed in claim 19, wherein the first line section of at least one of the at least one drive line and the at least one detection line are coupled to the second line section of at least one of the at least one drive line and the at least one detection line by means of at least one electrical contact-connection element arranged in a manner essentially running vertically with respect to the substrate.

21. The biosensor array as claimed in claim 17, wherein at least one of the at least one drive line and the at least one detection line is formed in a manner running on an underside of the substrate or beneath the substrate.

22. The biosensor array as claimed in claim 7, wherein the drive unit has a supply unit that is common to all the biosensor zones and can be used to apply the electrical drive signal to the at least one selected biosensor zone.

23. The biosensor array as claimed in claim 22, wherein at least one of the drive unit and the detection unit are set up such that an electrical reference Signal can be applied to at least a portion of the nonselected biosensor zones.

24. The biosensor array as claimed in claim 12, wherein the drive unit has, for a respective group of biosensor zones, a supply unit that is associated with the respective group and can be used to apply the electrical drive signal to the biosensor zones of the associated group.

25. The biosensor array as claimed in claim 7, wherein the detection unit has a measuring unit that is common to all the biosensor zones and can be used to detect the electrical detection signal at precisely one selected biosensor zone.

26. The biosensor array as claimed in claim 12, wherein the detection unit has, for a respective group of biosensor zones, a measuring unit that is associated with the respective group, and each of the measuring units can be used to detect the electrical detection signal at precisely one selected biosensor zone of the associated group.

27. The biosensor array as claimed in claim 7, further comprising a potentiostat device that can be used to predefine a constant electrical potential for at least a portion of the biosensor zones.

28. The biosensor array as claimed in claim 27, wherein the potentiostat device has a reference electrode, a counterelectrode, and an operational amplifier, and wherein a first input of the operational amplifier is coupled to the reference electrode, a second input of the operational amplifier is coupled to a reference potential, and an output of the operational amplifier is coupled to the counterelectrode.

29. The biosensor array as claimed in claim 7, wherein the selection unit includes a first switching unit configured to selectively activate and deactivate the drive lines and a second switching unit configured to selectively activate and deactivate the detection lines.

30. A biosensor array, comprising:

a substrate;

a plurality of biosensor zones arranged on the substrate, each biosensor zone including a first sensor electrode and a second sensor electrode configured such that capture molecules can be immobilized thereon and a first terminal directly electrically connected to the first sensor electrode and a second terminal directly electrically connected to the second sensor electrode of each biosensor zone;

at least one first signal line and at least one second signal line, wherein the at least one first signal line is electrically insulated from the at least one second signal line;

wherein in each case the first terminal of each biosensor zone is coupled to precisely one of the at least one first signal line and the second terminal of each biosensor zone is coupled to precisely one of the at least one second signal line, the at least one drive line and the at least one detection line being separate lines, and at least one of the at least one first signal line and at least one of the at least one second signal line is coupled to at least two of the biosensor zones;

a first drive unit configured to provide a first electrical drive signal and a second drive unit configured to provide a second electrical drive signal;

at least one of a first detection unit coupled to the first drive unit and a second detection unit coupled to the second drive unit, which detects or detect at least one of a first and a second electrical detection signal of a selected biosensor zone that results from the first and the second electrical drive signal; and a selection unit configured to couple the first drive unit to the first signal line of a biosensor zone to be selected and the second drive unit to the second signal line of the biosensor zone to be selected, whereby the biosensor zone is selected.

31. The biosensor array as claimed in claim 30, further comprising an evaluation unit configured to determine for the at least one selected biosensor zone on the basis of at least one of the first and the second detection signal at least one of whether sensor events have taken place at the at least one selected biosensor zone and the quantity in which sensor events have taken place at the at least one selected biosensor zone.

32. The biosensor array as claimed in claim 30, wherein at least one of the biosensor zones is an electrochemical biosensor zone.

33. The biosensor array as claimed in claim 32, wherein at least one of the biosensor zones is a redox recycling biosensor zone.

34. The biosensor array as claimed in claim 30, wherein at least one of the biosensor zones has a first and a second electrode, the first electrode being coupled to the first terminal and the second electrode being coupled to the second terminal of the at least one biosensor zone.

35. The biosensor array as claimed in claim 34, wherein the first and the second electrodes are interdigital electrodes.

36. The biosensor array as claimed in claim 30, wherein the biosensor zones are grouped to form a plurality of biosensor groups such that each biosensor group can optionally be operated separately from the other biosensor groups or jointly with at least a portion of the other biosensor groups.

37. The biosensor array as claimed in claim 30, wherein the substrate is a ceramic substrate, a semiconductor substrate, a glass substrate, or a plastic substrate.

38. The biosensor array as claimed in claim 30, wherein the first and the second electrical drive signals are electrical DC voltage signals having a different sign, and wherein at least one of the first and the second electrical detection signal is an electric current.

39. The biosensor array as claimed in claim 30, wherein the values of the first and of the second electrical drive signals are set such that, on account of a sensor event that has taken place at a biosensor zone, at least one of a significant first and second detection signal is generated essentially only when the first terminal of the biosensor zone is coupled to the first drive unit and the second terminal of the biosensor zone is coupled to the second drive unit.

40. The biosensor array as claimed in claim 31, wherein, integrated in the substrate is at least one of the following:
   an analog-to-digital converter circuit, which can convert an analog electrical signal into a digital signal and provide the digital signal to the evaluation unit;
   an electrical supply unit, which can provide at least one of electrical voltage signals and electric current signals to at least one of the first drive unit, the second drive unit and the selection unit;
   a digital-to-analog converter circuit, which can convert a digital signal of the supply unit into an analog signal and provide the analog signal to at least one of the drive unit and the selection unit; an input/output interface; and an amplifier unit configured to amplify at least one of the first and the second electrical detection signal.

41. The biosensor array as claimed in claim 30, wherein the at least one first signal line and the at least one second signal line are at least partly formed in two different line planes that are at least one of in, on, and below the substrate.

42. The biosensor array as claimed in claim 41, wherein the biosensor zones are formed in precisely one of the line planes.

43. The biosensor array as claimed in claim 41, wherein, in a first line section, in which the at least one first signal line and the at least one second signal line are free of a mutual crossover, the at least one first signal line and the at least one second signal line are formed such that they run in the same plane, and in which, in a second line section, in which the at least one first signal line and the at least one second signal line mutually cross one another, the at least one first signal line and the at least one second signal line are formed such that they run in different planes.

44. The biosensor array as claimed in claim 43, wherein the first line section of at least one of the at least one first signal line and the at least one second signal line are coupled to the second line section of at least one of the at least one first signal line and the at least one second signal line by means of at least one electrical contact-connection element arranged in a manner essentially running vertically with respect to the substrate.

45. The biosensor array as claimed in claim 41, wherein at least one of the at least one first signal line and the at least one second signal line is formed in a manner running on an underside of the substrate or beneath the substrate.

46. The biosensor array as claimed in claim 30, wherein at least one of the first drive unit has a first supply unit that is common to all the biosensor zones and the second drive unit has a second supply unit that is common to all the biosensor zones, wherein at least one of the first supply unit can be used to apply the first electrical drive signal to the at least one selected biosensor zone, and the second supply unit can be used to apply the second electrical drive signal to the at least one selected biosensor zone.

47. The biosensor array as claimed in claim 46, wherein the first and second drive units are set up such that an electrical reference signal can be applied to at least a portion of the nonselected biosensor zones, the value of said electrical reference signal essentially being the average value of the first and the second drive signals.

48. The biosensor array as claimed in claim 30, wherein at least one of the first drive unit has, for a respective first group of biosensor zones, a first supply unit that is associated with the respective group, which first supply unit can be used to apply the first electrical drive signal to the biosensor zones of the associated first group, and the second drive unit has, for a respective second group of biosensor zones, a second supply unit that is associated with the respective group, which second supply unit can be used to apply the second electrical drive signal to the biosensor zones of the associated second group.

49. The biosensor array as claimed in claim 30, wherein at least one of the first detection unit has a first measuring unit that is common to all the biosensor zones, which first measuring unit can be used to detect the electrical first detection signal at precisely one selected biosensor zone, and the second detection unit has a second measuring unit that is common to all the biosensor zones, which second measuring unit can be used to detect the electrical second detection signal at precisely one selected biosensor zone.

50. The biosensor array as claimed in claim 48, wherein at least one of the first detection unit has, for a respective third group of biosensor zones, a first measuring unit that is associated with the respective third group, wherein each of the first measuring units can be used to detect the electrical first detection signal at precisely one selected biosensor zone of the associated third group, and the second detection unit has, for a respective fourth group of biosensor zones, a second measuring unit that is associated with the respective fourth group, wherein each of the second measuring units can be used to detect the electrical second detection signal at precisely one selected biosensor zone of the associated fourth group.

51. The biosensor array as claimed in claim 30, further comprising a potentiostat device that can be used to predefine a constant electrical potential for an electrolyte introduced into at least a portion of the biosensor zones.

52. The biosensor array as claimed in claim 51, wherein the potentiostat device has a reference electrode, a counterelectrode, and an operational amplifier, wherein a first input of the operational amplifier is coupled to the reference electrode, a second input of the operational amplifier is coupled to a reference potential, and an output of the operational amplifier is coupled to the counterelectrode.

53. The biosensor array as claimed in claim 30, wherein the selection unit includes a first switching unit configured to selectively activate and deactivate the drive lines and a second switching unit configured to selectively activate and deactivate the detection lines.

* * * * *